US012611640B2

(12) United States Patent
Ramsay et al.

(10) Patent No.: US 12,611,640 B2
(45) Date of Patent: *Apr. 28, 2026

(54) CONTINUOUS FLOW MICROFLUIDIC SYSTEM

(71) Applicant: The University of British Columbia, Vancouver (CA)

(72) Inventors: Euan Ramsay, Vancouver (CA); Robert James Taylor, Vancouver (CA); Timothy Leaver, Delta (CA); Andre Wild, Vancouver (CA); Kevin Ou, Toronto (CA); Colin Walsh, Belmont, CA (US)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/434,638

(22) Filed: Feb. 6, 2024

(65) Prior Publication Data

US 2024/0335803 A1 Oct. 10, 2024

Related U.S. Application Data

(63) Continuation of application No. 17/127,777, filed on Dec. 18, 2020, now Pat. No. 11,938,454, which is a (Continued)

(51) Int. Cl.

*B01F 25/431* (2022.01)
*A61K 9/16* (2006.01)

(Continued)

(52) U.S. Cl.

CPC ...... *B01F 25/43161* (2022.01); *A61K 9/1682* (2013.01); *B01F 25/4323* (2022.01);

(Continued)

(58) Field of Classification Search

None

See application file for complete search history.

(56) References Cited

U.S. PATENT DOCUMENTS

| | | | |
|---|---|---|---|
| 3,394,924 | A | 7/1968 | Harder |
| 3,404,869 | A | 10/1968 | Harder |

(Continued)

FOREIGN PATENT DOCUMENTS

| | | | |
|---|---|---|---|
| CA | 2 918 368 | A1 | 1/2015 |
| CA | 2 927 358 | A1 | 4/2015 |

(Continued)

OTHER PUBLICATIONS

Office Action mailed Jul. 8, 2024, in corresponding Japanese application No. 2023-97192, filed Aug. 24, 2016, 9 pages.

(Continued)

*Primary Examiner* — Lore R Jarrett

(74) *Attorney, Agent, or Firm* — Christensen O'Connor Johnson Kindness PLLC

(57) ABSTRACT

The present disclosure is directed towards improved systems and methods for large-scale production of nanoparticles used for delivery of therapeutic material. The apparatus can be used to manufacture a wide array of nanoparticles containing therapeutic material including, but not limited to, lipid nanoparticles and polymer nanoparticles. In certain embodiments, continuous flow operation and parallelization of microfluidic mixers contribute to increased nanoparticle production volume.

20 Claims, 16 Drawing Sheets

Related U.S. Application Data continuation of application No. 15/552,473, filed as application No. PCT/US2016/019414 on Feb. 24, 2016, now abandoned.

(60) Provisional application No. 62/275,630, filed on Jan. 6, 2016, provisional application No. 62/120,179, filed on Feb. 24, 2015.

(51) Int. Cl.

| | |
|---|---|
| ***B01F 25/432*** | (2022.01) |
| ***B01F 25/433*** | (2022.01) |
| ***B01F 33/30*** | (2022.01) |
| ***B01F 33/81*** | (2022.01) |
| ***B01F 101/22*** | (2022.01) |
| ***B01J 19/00*** | (2006.01) |
| ***G01N 15/00*** | (2024.01) |
| ***G01N 35/00*** | (2006.01) |

(52) U.S. Cl.

CPC .......... *B01F 25/4331* (2022.01); *B01F 33/30* (2022.01); *B01F 33/813* (2022.01); *B01J 19/0093* (2013.01); *B01F 25/43172* (2022.01); *B01F 25/431971* (2022.01); *B01F 2101/22* (2022.01); *B01J 2219/00783* (2013.01); *B01J 2219/00822* (2013.01); *B01J 2219/00824* (2013.01); *B01J 2219/00831* (2013.01); *B01J 2219/00833* (2013.01); *B01J 2219/00855* (2013.01); *B01J 2219/00858* (2013.01); *B01J 2219/0086* (2013.01); *B01J 2219/00869* (2013.01); *B01J 2219/00873* (2013.01); *B01J 2219/00889* (2013.01); *B01J 2219/00894* (2013.01); *B01J 2219/00898* (2013.01); *B01J 2219/00986* (2013.01); *G01N 2015/0038* (2013.01); *G01N 2035/00158* (2013.01)

(56) References Cited

U.S. PATENT DOCUMENTS

| | | | |
|---|---|---|---|
| 3,574,485 | A | 4/1971 | Herman, Jr. |
| 3,855,368 | A | 12/1974 | Prochazka et al. |
| 3,927,868 | A | 12/1975 | Moore |
| 4,027,857 | A | 6/1977 | Cunningham |
| 4,629,589 | A | 12/1986 | Gupta et al. |
| 4,732,585 | A | 3/1988 | Lerner |
| RE33,444 | E | 11/1990 | Lerner |
| 5,335,992 | A | 8/1994 | Holl |
| 6,331,072 | B1 | 12/2001 | Schierholz et al. |
| 6,399,031 | B1 | 6/2002 | Herrmann et al. |
| 6,457,854 | B1 | 10/2002 | Koop et al. |
| 9,142,662 | B2 | 9/2015 | Ryu et al. |
| 9,500,664 | B2 | 11/2016 | Ness et al. |
| 10,076,730 | B2 | 9/2018 | Wild et al. |
| 10,520,137 | B2 | 12/2019 | Tanaka et al. |
| 11,938,454 | B2 | 3/2024 | Ramsay et al. |
| 12,434,206 | B2 * | 10/2025 | Schöck .................. B01F 23/47 |
| 2002/0023841 | A1 | 2/2002 | Ahn et al. |
| 2002/0187074 | A1 | 12/2002 | O'Connor et al. |
| 2003/0040105 | A1 | 2/2003 | Sklar et al. |
| 2004/0037161 | A1 | 2/2004 | Honda et al. |
| 2004/0191086 | A1 | 9/2004 | Paukovits, Jr. et al. |
| 2004/0238355 | A1 | 12/2004 | Kimizuka |
| 2004/0248291 | A1 | 12/2004 | Yamamoto et al. |
| 2004/0252584 | A1 | 12/2004 | Ji et al. |
| 2004/0265184 | A1 | 12/2004 | Matsuda et al. |
| 2006/0087048 | A1 | 4/2006 | Mello et al. |
| 2006/0101775 | A1 | 5/2006 | Miyake et al. |
| 2006/0171864 | A1 | 8/2006 | Caze et al. |
| 2006/0280029 | A1 | 12/2006 | Garstecki et al. |
| 2006/0285433 | A1 * | 12/2006 | Yang .................. B01F 25/4338 366/DIG. 3 |
| 2007/0017633 | A1 | 1/2007 | Tonkovich et al. |
| 2007/0081923 | A1 | 4/2007 | Choe et al. |
| 2007/0089460 | A1 | 4/2007 | Lindig et al. |
| 2007/0225532 | A1 | 9/2007 | Tonkovich et al. |
| 2009/0087509 | A1 | 4/2009 | Linares |
| 2009/0142846 | A1 | 6/2009 | Crenshaw et al. |
| 2010/0022680 | A1 | 1/2010 | Karnik et al. |
| 2011/0003325 | A1 | 1/2011 | Durack |
| 2011/0128814 | A1 | 6/2011 | Hanada |
| 2011/0315227 | A1 | 12/2011 | Shu |
| 2012/0085644 | A1 | 4/2012 | Renzi et al. |
| 2012/0115755 | A1 | 5/2012 | Oh et al. |
| 2012/0121481 | A1 | 5/2012 | Romanowsky et al. |
| 2012/0174772 | A1 * | 7/2012 | Knobel ................ B01F 25/433 95/45 |
| 2012/0214224 | A1 | 8/2012 | Chan |
| 2012/0244529 | A1 | 9/2012 | Fuchs et al. |
| 2012/0276209 | A1 | 11/2012 | Cullis et al. |
| 2012/0300576 | A1 | 11/2012 | Li et al. |
| 2012/0307589 | A1 | 12/2012 | Hanada et al. |
| 2013/0236375 | A1 | 9/2013 | Tan et al. |
| 2013/0260474 | A1 | 10/2013 | Chan et al. |
| 2014/0038214 | A1 | 2/2014 | Neeves et al. |
| 2015/0025461 | A1 | 1/2015 | Corso et al. |
| 2015/0297834 | A1 | 10/2015 | Buder et al. |
| 2016/0022580 | A1 | 1/2016 | Ramsay et al. |
| 2016/0068883 | A1 | 3/2016 | Luo et al. |
| 2016/0130640 | A1 | 5/2016 | Wright et al. |
| 2024/0100492 | A1 * | 3/2024 | Wild .................. B01F 35/1452 |

FOREIGN PATENT DOCUMENTS

| | | | |
|---|---|---|---|
| CN | 102151504 | A | 8/2011 |
| CN | 201959734 | U | 9/2011 |
| CN | 102753257 | A | 10/2012 |
| CN | 103906503 | A | 7/2014 |
| DE | 2448350 | A1 | 4/1975 |
| DE | 103 56 308 | A1 | 6/2005 |
| EP | 2431090 | A1 | 3/2012 |
| EP | 3797860 | A1 | 3/2021 |
| JP | 2008246283 | A | 10/2008 |
| JP | 2009166039 | A | 7/2009 |
| JP | 2011183381 | A | 9/2011 |
| JP | 2012520174 | A | 9/2012 |
| JP | 2014517513 | A | 7/2014 |
| JP | 2015502337 | A | 1/2015 |
| JP | 2023097192 | A | 7/2023 |
| KR | 20100060476 | A | 6/2010 |
| KR | 10-2012-0013320 | B1 | 2/2012 |
| KR | 20130043777 | A | 5/2013 |
| WO | 2008/039209 | A1 | 4/2008 |
| WO | 2010/131297 | A1 | 11/2010 |
| WO | 2013111789 | A1 | 8/2013 |
| WO | 2014172045 | A1 | 10/2014 |

OTHER PUBLICATIONS

International Search Report and Written Opinion mailed May 17, 2016, issued in corresponding International Application No. PCT/US16/19414, filed Feb. 24, 2016, 20 pages.

International Preliminary Report on Patentability mailed Nov. 9, 2017, issued in corresponding International Application No. PCT/US2016/029879, filed Apr. 28, 2016, 15 pages.

Partial Search Report and Invitation to Pay Additional Fees mailed Sep. 21, 2018, issued in corresponding European Application No. 16756307.1, filed Feb. 24, 2016, 23 pages.

Extended European Search Report mailed Dec. 14, 2018, issued in corresponding European Application No. 16787188.8, filed Apr. 28, 2016, 9 pages.

Extended European Search Report mailed Feb. 8, 2019, issued in corresponding European Application No. 16756307.1, filed Feb. 24, 2016, 17 pages.

First Office Action mailed Jun. 24, 2019, issued in corresponding Chinese Application No. 201680022904.1, filed Feb. 24, 2016, 6 pages.

(56) References Cited

OTHER PUBLICATIONS

Search Report mailed mailed Jun. 24, 2019, issued in corresponding Chinese Application No. 201680022904.1, filed Feb. 24, 2016, 3 pages.
Supplementary European Search Report mailed Aug. 1, 2019, issued in corresponding European Application No. 16882817.6, filed Aug. 24, 2016, 9 pages.
Chen et al., "Optimal Designs of Staggered Dean Vortex Micromixers," International Journal of Molecular Sciences 12(6):3500-3524, Jan. 11, 2011.
Machine translation of Notice of Reasons for Refusal, mailed Dec. 24, 2019, issued in related Japanese Application No. 2017-544579, filed Feb. 24, 2016, 11 pages.
Final Office Action, mailed Dec. 9, 2019, issued in related U.S. Appl. No. 16/102,518, filed Aug. 13, 2016, 5 pages.
Deshpande, A., "Polystyrene Properties," Buzzle, Feb. 1, 2013, <http://www.buzzle.com/articles /polystyreneproperties.html> [retrieved Jul. 11, 2016], pp. 1-6; especially p. 3, table entitled "Mechanical Properties."
Howell, P.B. Jr., et al., "Design and Evaluation of a Dean Vortex-Based Micromixer," Lab on a Chip 4(6):663-669, Dec. 2004.
International Search Report and Written Opinion mailed Sep. 2, 2016, issued in corresponding International Application No. PCT/US2016/29879, filed Apr. 28, 2016, 18 pages.
International Search Report and Written Opinion mailed Nov. 2, 2016, issued in corresponding International Application No. PCT/CA2016/050997, filed Aug. 24, 2016, 6 pages.
International Preliminary Report on Patentability mailed Aug. 29, 2017, issued in corresponding International Application No. PCT/US2016/019414, filed Feb. 24, 2016, 12 pages.
Non-Final Office Action, mailed Jun. 28, 2019, issued in related United States U.S. Appl. No. 16/102,518, filed Aug. 13, 2016, 7 pages.
First Office Action, mailed on May 19, 2020, issued in corresponding Chinese Application No. 201680031630.2, filed Apr. 28, 2016, 26 pages.
Canadian Examination Report as mailed on Mar. 31, 2023, from Canadian Application No. 2,977,768, filed Jun. 9, 2022, 3 pages.
Office Action mailed on Mar. 3, 2023, issued in corresponding European Application No. 20 207 659.2, filed on Aug. 24, 2016, 5 pages.
Office Action mailed on Mar. 13, 2023, issued in corresponding Japanese Application No. 2018-535128 (Japanese version), filed on Aug. 24, 2016, 19 pages.
Korean Office Action mailed on Aug. 23, 2022, issued in corresponding Korean Application No. 10-2017-7026948, filed on Feb. 24, 2016, 33 pages.
Canadian Examination Report mailed on Apr. 16, 2021, issued in corresponding Canadian Application No. 3009691, filed on Aug. 24, 24, 2016, 4 pages.
Third Chinese Office Action mailed on Jun. 10, 2021, issued in corresponding Chinese Application No. 201680083280.4, filed on Aug. 24, 2016, 7 pages.
Second Japanese Office Action mailed on May 10, 2021, issued in corresponding Japanese Application No. 2018-535128, filed on Aug. 24, 2016, and its English translation thereof, 6 pages.
Third Chinese Office Action mailed on May 8, 2021, issued in corresponding Chinese Application No. 201680031630.2, filed on Apr. 28, 2016, and it English translation thereof, 21 pages.
Examination Report mailed Jun. 24, 2020, issued in Australian Application No. 2016222746, filed on Feb. 24, 2016, 4 pages.
Office Action mailed Jul. 13, 2020, issued in Chinese Application No. 201680083280.4, filed on Aug. 24, 2016, and its English translation thereof, 15 pages.
Office Action mailed Dec. 9, 2020, issued in Chinese Application No. 201680031630.0, filed on Apr. 28, 2016, and its English translation thereof, 53 pages.
Office Action mailed Aug. 14, 2020, issued in Chinese Application No. 201680022904.1, filed on Feb. 24, 2016, and its English translation thereof, 18 pages.
Examination Report mailed Jan. 20, 2021, issued in European Application No. 16756307.1, filed on Feb. 24, 2016, 5 pages.
European Search Report mailed Mar. 2, 2021, issued in European Application No. 20207659.2, filed on Aug. 24, 2016, 21 pages.
Extended European Search Report mailed Mar. 25, 2025, issued in corresponding European Application No. EP24212380, filed Feb. 24, 2016, 9 pages.

* cited by examiner

CONTINUOUS FLOW MICROFLUIDIC SYSTEM

CROSS-REFERENCE TO RELATED APPLICATIONS

This application is a continuation of U.S. patent application Ser. No. 17/127,777, filed Dec. 18, 2020, which is a continuation of U.S. patent application Ser. No. 15/552,473, filed Aug. 21, 2017, which is a national phase application of International Application No. PCT/US2016/019414, filed Feb. 24, 2016, which claims the benefit of U.S. Patent Application No. 62/120,179, filed Feb. 24, 2015, and U.S. Patent Application No. 62/275,630, filed Jan. 6, 2016, the disclosures of which are hereby incorporated by reference in their entirety.

BACKGROUND

The manufacture of pharmaceutical compositions on a large-scale for clinical development and commercial production has traditionally been challenging. Often techniques used in the laboratory for small-scale production of pharmaceuticals are not amenable to scale-up. These challenges are exacerbated when manufacturing complex pharmaceutical colloidal systems such as nanoparticles. Nanoparticles comprise multiple components, including, but not limited to, lipids, polymers, low molecular weight compounds, nucleic acids, proteins, peptides, and imaging agents, including inorganic molecules. Traditional processes for the manufacture of nanoparticles are batch-based systems and often results in production of meta-stable nanoparticles where particle characteristics such as size, polydispersity and encapsulation efficiency are sensitive to (local) environmental changes within the batch manufacturing process, including, but not limited to, temperature, pH, ionic strength, buffer composition, solvent concentrations. Consequently, traditional batch processes for the manufacture of nanoparticles are expensive, time consuming, and difficult to reproduce, which necessitates substantial optimization with increases in batch sizes leading to increased commercial risk. Moreover, traditional nanoparticle manufacturing processes necessitate nanoparticle product contact with the manufacturing apparatus, which requires costly and time-consuming cleaning and sterilization validation because it is not economically viable to dispose of the apparatus after manufacture of each batch.

In view of these challenges, improved nanoparticle manufacturing systems that yield greater production volume are desirable.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a system for continuous flow operation of a microfluidic chip is provided. In one embodiment, the system includes:

(1) a microfluidic chip, comprising:
- (a) a first inlet configured to receive a first solution;
- (b) a second inlet configured to receive a second solution; and

- (c) a first mixer, comprising:
  - (i) a first inlet microchannel configured to receive the first solution from the first inlet;
  - (ii) a second inlet microchannel configured to receive the second solution from the second inlet; and
  - (iii) a mixing microchannel configured to mix the first solution and the second solution to provide a nanoparticle solution at a mixer outlet; and
- (d) a chip outlet in fluid communication with the mixer outlet through a nanoparticle solution microchannel;

(2) a first continuous flow fluid driver configured to continuously drive the first solution from a first solution reservoir into the first inlet of the microfluidic chip;

(3) a second continuous flow fluid driver configured to continuously drive the second solution from a second solution reservoir into the second inlet of the microfluidic chip; and (4) a system outlet in fluid communication with the chip outlet, wherein the system outlet is configured to output the nanoparticle solution.

In one aspect, a method of forming nanoparticles is provided. In one embodiment, the method comprises flowing a first solution and a second solution through a system according to the disclosed embodiment and forming a nanoparticle solution in the first mixer of the microfluidic chip.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 11 is a labeled photography of an exemplary 8× parallel microfluidic system with "horizontal" connections (i.e., extending parallel to the major plane of the devices) that includes two continuous flow pumps and eight microfluidic mixing chips coupled to two inlet manifolds and one outlet manifold.

DETAILED DESCRIPTION

The present disclosure is directed towards improved systems and methods for large-scale production of nanoparticles used for delivery of therapeutic material. The apparatus can be used to manufacture a wide array of nanoparticles containing therapeutic material including, but not limited to, lipid nanoparticles and polymer nanoparticles. In certain embodiments, continuous flow operation and parallelization of microfluidic mixers contribute to increased nanoparticle production volume. While the present description is primarily directed to the manufacture of nanoparticles through mixing solutions, it will be appreciated that the devices, systems, and methods, are generally applicable beyond these applications. Therefore, the mixing of two or more solutions of any composition are contemplated by the disclosed embodiments.

Microfluidic mixers are microfluidic elements that are integrated into microfluidic devices on a microfluidic chip. As used herein, a microfluidic chip is defined as a platform comprising one or more microfluidic devices disposed therein, as well as inlets and outlets for connecting fluid inputs and outputs to the microfluidic devices. The microfluidic devices are defined as microfluidic elements that include at least one inlet, one outlet, and one portion that performs a fluidic function, such as mixing, heating, filtering, reacting, etc. In several exemplary embodiments disclosed herein, the microfluidic devices described are microfluidic mixing devices configured to mix a first solution with a second solution in a mixer to provide a mixed solution. However, other microfluidic devices are also compatible with the disclosed systems.

In particular, the present disclosure provides a continuous flow apparatus for the manufacture of nanoparticles, which enables the simple, rapid and reproducible manufacture of nanoparticles from small-scale (e.g., less than 50 mL) production for pre-clinical development, to large-scale production (e.g., greater than 1000 L) for clinical development and commercial supply. Moreover, the present disclosure employs microfluidics which has the advantage of exquisite control over environmental factors during manufacture, and microfluidics possesses the further advantage that increased output is enabled by parallelization of the microfluidic mixers without the need for further process optimization. The number of microfluidic mixers in parallel is dictated by the batch size requirements, and the desired time frame for manufacture of the batch. In further embodiments, the present disclosure provides a continuous flow scale-up apparatus for the manufacture of nanoparticles with a fully disposable fluid path. The fully disposable fluid path enables a user eliminating expensive and time-consuming cleaning validation protocols for GMP manufacture.

Figure 1:
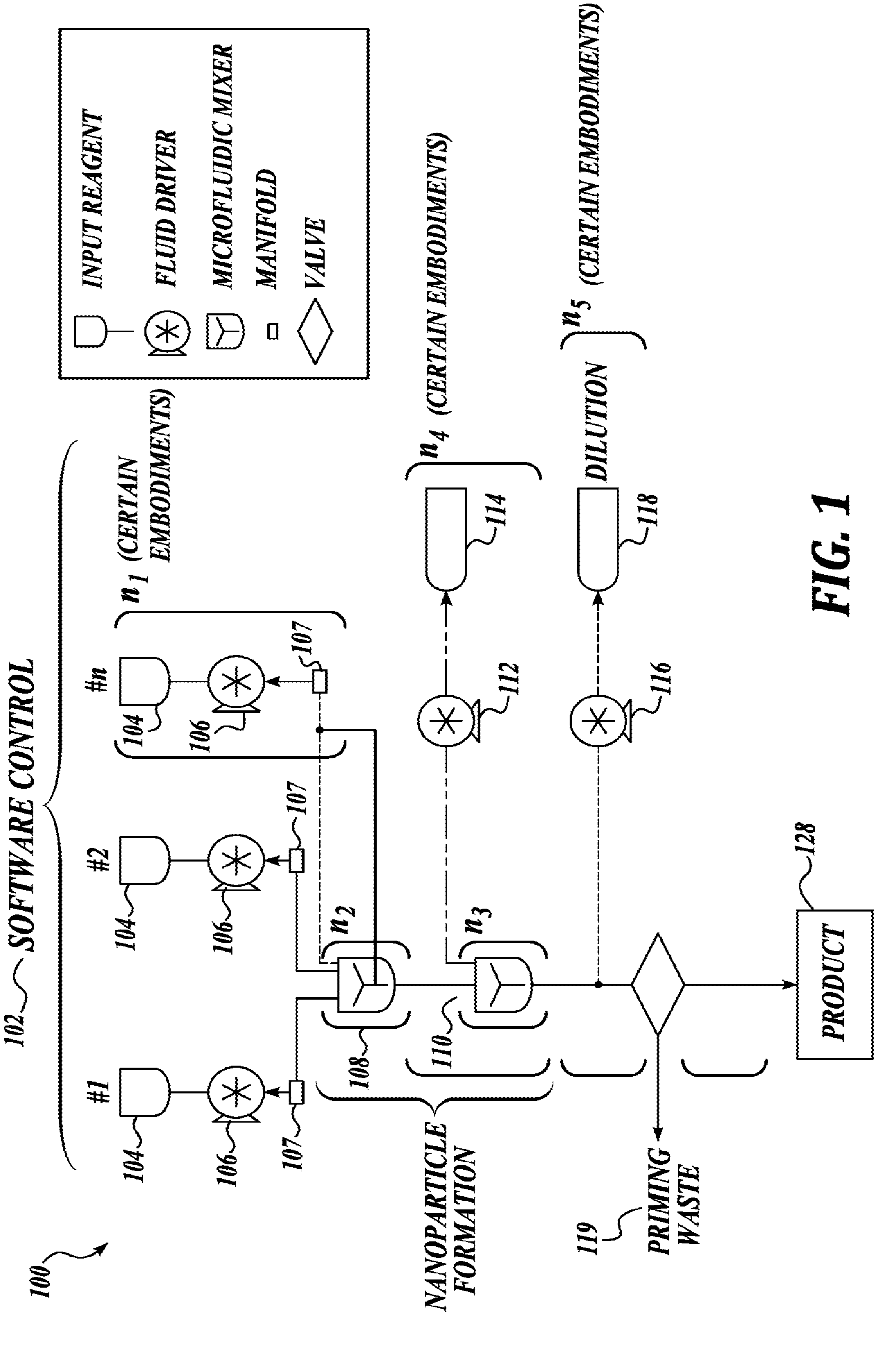
FIG. 1 is a schematic representation of a continuous flow system of the present disclosure.

FIG. 1 is a schematic representation of the scope of the present disclosure, a continuous flow microfluidic-based manufacturing apparatus for large-scale nanoparticle production. The representative system 100 uses software systems 102 to control manufacturing parameters such as, but not limited to, fluid flow rate, the ratio of the flow rate for the independent fluid streams, pressure within the apparatus, and temperature control. The apparatus 100 includes two or more ($n_1$) independent fluid inlet streams driven by fluid drivers 106 (e.g., pumps) to provide flow of nanoparticle and therapeutic materials from reservoirs 104 into manifold systems 107 that split the continuous flow streams and equal flow is driven to the inlets of each microfluidic mixer contained within the parallelized microfluidic mixer array 108. The number of microfluidic mixers ($n_2$) is scaled depending on throughput requirements. In one embodiment, the number of mixers is 2 or greater. In one embodiment, the number of mixers is 2. In one embodiment, the number of mixers is 3 or greater. In one embodiment, the number of mixers is 3. In one embodiment, the number of mixers is 4 or greater. In one embodiment, the number of mixers is 4. In one embodiment, the number of mixers is 8 or greater. In one embodiment, the number of mixers is 8. In one embodiment, the number of mixers is 10 or greater. In one embodiment, the number of mixers is 10. In one embodiment, the number of mixers is 20 or greater.

In certain embodiment, after mixer array 108, one or more ($n_3$) post-formation microfluidic mixers 110 are arranged in sequence so that one or more additional components ($n_4$) (e.g., targeting ligands) can be added to the nanoparticles emerging from the initial microfluidic mixer array 108 or so that rapid buffer exchange or dilution can occur directly following nanoparticle manufacture. The post-formation microfluidic mixer(s) 110 can also be in parallel, as with mixer array 108, and are fed materials from reservoir 114 via continuous flow from a fluid driver 112.

Nanoparticles are formed via nanoprecipitation due to rapid mixing of the fluid streams within the mixer array 108. In one embodiment, the outlet streams from the microfluidic mixer array 108, or post-formation microfluidic mixer(s) 110, is merged back into a single stream (e.g., using a manifold) and the resulting nanoparticles/aqueous/organic mixture is subsequently diluted with one or more ($n_5$) streams of aqueous reagent 118 delivered via fluid driver 116 to stabilize the nanoparticle product before further processing. The dilution step can be achieved by in-line dilution where the aqueous buffer contacts directly with the output stream. Alternatively, dilution can be achieved using a further microfluidic mixer array as part of the post-formation microfluidic mixer(s) 110. One additional benefit in the continuous flow process is that a time delay in diluting particle product can influence particle quality and stability. Accordingly, the tubing length and hold-up volume between mixer and dilution can be tuned to allow for adequate time for particles to "mature" before being diluted. Tubing acts as an accumulator to collect and hold product prior to dilution (for a "hold time"). In one embodiment, the distance between the last mixer (e.g., 108 or 110) and the dilution junction is about 1 cm to about 50 cm. In one embodiment, the distance between the last mixer (e.g., 108 or 110) and the dilution junction is about 1 cm to about 10 cm. In one embodiment, the distance between the last mixer (e.g., 108 or 110) and the dilution junction is about 10 cm to about 50 cm.

In another embodiment, the system, including tubing dimensions and flow characteristics, are configured to produce a specific hold time. In one embodiment, the hold time is about 5 seconds to about 1 hour. In one embodiment, the hold time is about 30 minutes to about 1 hour. In one embodiment, the hold time is about 5 seconds to about 60 seconds. In one embodiment, the hold time is about 5 seconds to about 10 seconds. In one embodiment, the hold time is greater than about 5 seconds. In one embodiment, the hold time is greater than about 10 seconds. In one embodiment, the hold time is greater than about 60 seconds. In one embodiment, the hold time is greater than about 10 minutes. In one embodiment, the hold time is greater than about 30 minutes. In one embodiment, the hold time is greater than about 45 minutes.

A valve directs flow to waste collection 119 prior to the system reaching steady state when the valve is configured such that flow is directed to final nanoparticle product collection 128.

In certain embodiments nanoparticle manufacturing is conducted in a specialized barrier facility that eliminates the requirement for filtration to ensure a sterile product.

Figure 2:
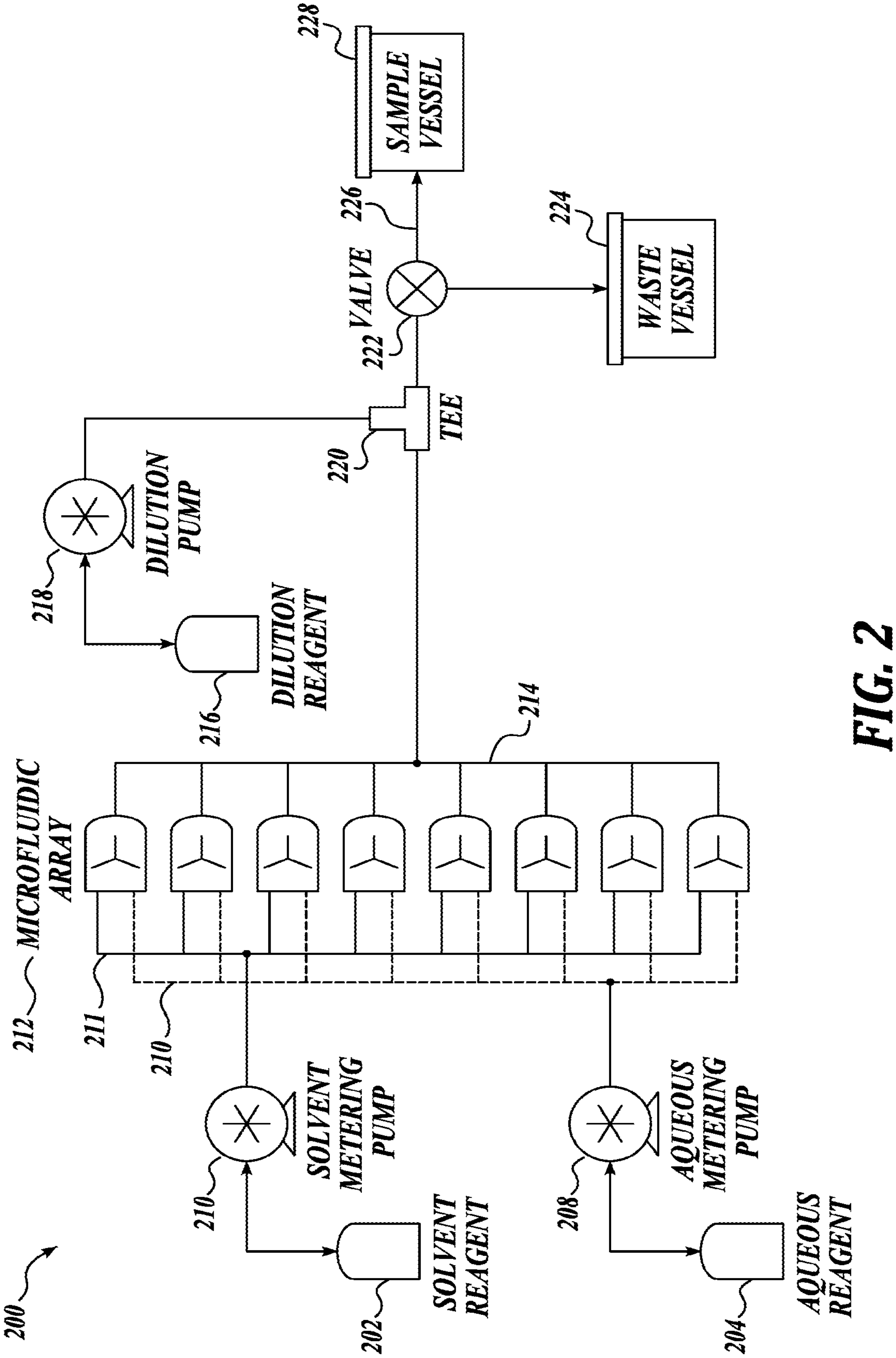
FIG. 2 is a schematic representation of a continuous flow system of the present disclosure.

FIG. 2 is a schematic of a representative system of the present disclosure, a continuous flow microfluidic-based manufacturing apparatus for large-scale nanoparticle production. The representative system 200 includes two fluid drivers 206, 208 to provide a continuous flow of aqueous buffer 204 and water-miscible organic containing dissolved lipids streams 202 through tubing 226 that connects the whole system. Manifolds 210 and 211 split the continuous flow streams and equal flow is driven to the inlets of each parallelized mixer. The number of microfluidic mixers is scaled depending on throughput requirements, and there are 8 mixers in the example 212). Nanoparticles are formed via nanoprecipitation due to rapid mixing of the aqueous and organic streams within the microfluidic mixers. The outlet streams from the 8 parallelized mixers are merged back into a single stream using a manifold 214 and the resulting nanoparticles/aqueous/organic mixture is subsequently diluted with aqueous reagent 216 pumped 218 through a tee connector 220 to stabilize the nanoparticle product before further processing. In one embodiment, the nanoparticles formed off each microfluidic mixer are analyzed for quality and desired characteristics prior to being merged into a final output stream. A valve at the tail end of the system 222 directs flow from waste collection 224 prior to the system reaching steady state when the flow is directed to sample collection 228). Fluid contacting materials in the scenario described may be re-used, or be a single-use disposable. Single-use disposable eliminates the need to perform cleaning and cleaning validation on fluid contacting parts thus saving significant time and resources.

FIG. 2 shows apparatus 200, one embodiment of the present disclosure. In one embodiment, the apparatus provides a system for the manufacture of lipid nanoparticles containing a nucleic acid. In another embodiment, the apparatus provides a system for the manufacture of limit size lipid nanoparticles including, but not limited to, liposomes and nanoemulsions containing therapeutic material. In a further embodiment, the apparatus provides a system for the manufacture of polymer nanoparticles containing therapeutic material.

In one aspect, a system for continuous flow operation of a microfluidic chip is provided. In one embodiment, the system includes:

(1) a microfluidic chip, comprising:
  (a) a first inlet configured to receive a first solution;
  (b) a second inlet configured to receive a second solution; and
  (c) a first mixer, comprising:
    (i) a first inlet microchannel configured to receive the first solution from the first inlet;
    (ii) a second inlet microchannel configured to receive the second solution from the second inlet; and
    (iii) a mixing microchannel configured to mix the first solution and the second solution to provide a nanoparticle solution at a mixer outlet; and
  (d) a chip outlet in fluid communication with the mixer outlet through a nanoparticle solution microchannel;
(2) a first continuous flow fluid driver configured to continuously drive the first solution from a first solution reservoir into the first inlet of the microfluidic chip;
(3) a second continuous flow fluid driver configured to continuously drive the second solution from a second solution reservoir into the second inlet of the microfluidic chip; and
(4) a system outlet in fluid communication with the chip outlet, wherein the system outlet is configured to output the nanoparticle solution.

The systems and methods will now be described in further detail.

Continuous Flow

Continuous flow allows for large volumes of product (e.g., nanoparticles) to be produced using microfluidics, which are traditionally low-volume production systems. The use of parallelization, described in more detail below, further increases production capacity when combined with continuous flow.

As used herein, the terms "continuous" and "continuously" refer to system flow operations of relatively constant flow rate over a long duration. The constant flow rate is not unvarying, but varies very little over extended operation. Variations in flow are referred to as "pulses" or "pulsation." The level of pulsation depends on the operating conditions (e.g., flow rate and backpressure) of the fluid driver. In one embodiment, the constant flow rate varies by +/−10% or less at 50 ml/min flow rate and 250 PSI backpressure. In a further embodiment, the constant flow rate is +/−4% or less at 50 mL/min flow rate and 250 PSI backpressure. These values are in the absence of any pulse dampener.

A pulse dampener is incorporated into the system in certain embodiments in order to minimize flow pulsation from one or more of the continuous flow fluid drivers.

In one embodiment, the pulse dampener(s) have a 3:1 reduction in flow pulsation (dependent on pump operating conditions). In one exemplary embodiment, the pulse dampener comprises a flexible PTFE membrane and stainless steel and polyetheretherketone as fluid contacting materials.

In one embodiment, the volume produced during continuous operation is at least 100 mL completed within a 10-minute duration. In a further embodiment, the volume produced during continuous operation is at least 100 mL completed within a 2.5-minute duration. In a further embodiment, the volume produced during continuous operation is at least 100 mL completed within a 1.3-minute duration The pressures experienced by the microfluidic devices are relatively high, due to the desire for high throughput and the necessary high flow rates. In one embodiment, the system operates at pressures up to 500 PSI. The peak pressure of the system is at the outlet of the pump. The backpressure at the pump outlet is the sum of the backpressure of each downstream component (tubing, manifold, chips, etc.). With regard to microfluidic elements in the system, the maximum pressure occurs at the inlets of the chip. The microfluidic chip inlet pressure can reach a maximum of 200 PSI. In one embodiment, the peak pressure on the microfluidic chip is from about 100 PSI to about 200 PSI. In one embodiment, the system operates at pressure of about 5 PSI to about 200 PSI.

In one embodiment, the system is capable of producing greater than 500 ml of product per hour per microfluidic mixer. In one embodiment, the system is capable of producing greater than 750 ml, of product per hour per microfluidic mixer. These production rates can be multiplied via parallelization in order to yield multiple liters of product per hour for a single system.

As a result of the miniaturization of production via microfluidics and the increased capacity afforded by continuous flow operation, the footprint of the systems disclosed is greatly reduced compared to known systems capable of producing similar volumes per unit time. As an example, the smallest commercially available batch system, the NanoAssemblr (manufactured by Precision Nanosystems Inc. of Vancouver, BC) is a microfluidic system with a small footprint. However, due to the slow nature of batch processing, in order to produce 1 L of nanoparticles in 80 minutes, 40 NanoAssemblrs would be required, which would result in a footprint of about 2 $m^2$. This is at least twice the footprint of even the most basic continuous flow system disclosed herein.

In one embodiment, the system has a footprint area of 1 $m^2$ or less. In one embodiment, the system has a footprint area of 0.8 $m^2$ or less. A photograph of a representative system having two pumps driving four microfluidic mixing chips (4×), each with a single mixer, is pictured in FIG. 10. The footprint of this system is about 0.8 $m^2$ and it can produce over 1 L of nanoparticle solution per hour. Further parallelization can improve this production rate even further while maintaining essentially the same footprint.

Figure 10:
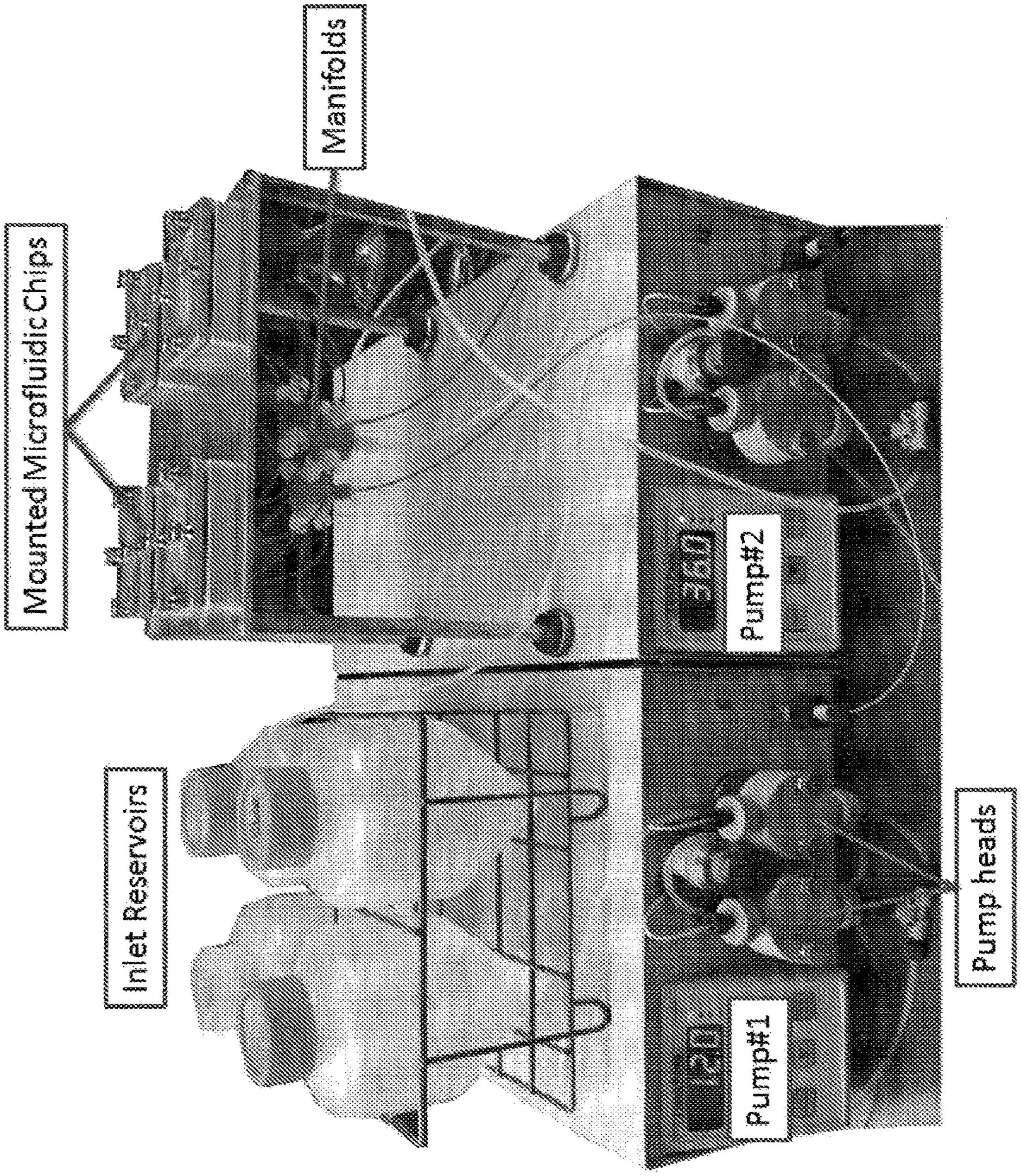
FIG. 10 is a labeled photograph of an exemplary 4× parallel microfluidic system with "vertical" connections (i.e., extending perpendicular to the major plane of the devices) that includes two continuous flow pumps and four microfluidic mixing chips coupled to inlet and outlet manifolds.

The system of FIG. 10 includes a flow ratio of 3:1 (Pump #2:Pump #1) and "vertical" connections (perpendicular to the major surface of the chips) between the manifolds and microfluidic chips.

Referring to FIG. 11, an 8× system is illustrated that is driven by two pumps. Two manifolds distribute the solutions to be mixed on the eight chips, each containing a single SHM mixing device similar to that illustrated in FIG. 6. A single third manifold receives the mixed solutions from the eight chips and concentrates them in a single stream for post-mixing processing, dilution, and/or product capture. The system of FIG. 11 is also distinct from that of FIG. 10 in that connections from the manifolds to the chips are in a "horizontal" configuration, parallel to the major surface of the chips. The horizontal configuration for connections is unexpectedly beneficial compared to vertical configuration. The vertical configuration would seem to be superior because each mixer assembly takes up less space. However, manipulation of the connections by a user becomes difficult in the confined space created by the vertical connectors. By using horizontal connectors, the connections are easily operable and more user-friendly.

In one embodiment, the system has a production volume of 0.76 L of nanoparticle solution per hour. In embodiments with multiple mixers (e.g., on the same microfluidic chip or separate microfluidic chips) the production volume can be increased by the number of mixers, N. For example, four mixers can produce a volume of 4×0.76 liters/hour. In another embodiment, the system has a production volume of 0.5 L of nanoparticle solution per hour. In another embodiment, the system has a production volume of 1.0 L of nanoparticle solution per hour.

In one embodiment, the system is scalable to produce a product solution from 0.025 L to 5000 L.

In one embodiment, the output of the system is limited only by the amount of starting material. That is, the system can produce product from the starting solutions as long as the starting solutions are available. Therefore, production volume in a single operating session is essentially unlimited by system constraints, due to the use of continuous flow.

Microfluidic Mixers

The microfluidic chips are configured to mix the first solution with the second solution through a mixing region. Many methods for this mixing process are known. In one embodiment, the mixing is chaotic advection. Compatible microfluidic mixing methods and devices are disclosed in:

(1) U.S. patent application Ser. No. 13/464,690, which is a continuation of PCT/CA2010/001766, filed Nov. 4, 2010, which claims the benefit of U.S. Ser. No. 61/280,510, filed Nov. 4, 2009;

(2) U.S. patent application Ser. No. 14/353,460, which is a continuation of PCT/CA2012/000991, filed Oct. 25, 2012, which claims the benefit of U.S. Ser. No. 61/551,366, filed Oct. 25, 2011;

(3) PCT/US2014/029116, filed Mar. 14, 2014 (published as WO 2014/172045, on Oct. 23, 2014), which claims the benefit of U.S. Ser. No. 61/798,495, filed Mar. 15, 2013;

(4) PCT/US2014/041865, filed Jul. 25, 2014 (published as WO 2015/013596, on Jan. 29, 2015), which claims the benefit of U.S. Ser. No. 61/858,973, filed Jul. 26, 2013;

(5) PCT/US2014/060961, which claims the benefit of U.S. Ser. No. 61/891,758, filed Oct. 16, 2013; and (6) U.S. Patent Application No. 62/275,630, filed Jan. 6, 2016, the disclosures of which are hereby incorporated by reference in their entirety. Furthermore, representative microfluidic devices are disclosed in further detail herein.

In certain embodiments, devices are provided for making nanoparticles of the type disclosed herein. The microfluidic devices are incorporated into the continuous flow systems and methods disclosed herein. In one embodiment, with reference to FIG. 6, the device includes:

(a) a first inlet 302 for receiving a first solution comprising a first solvent;

(b) a first inlet microchannel 304 in fluid communication with the first inlet to provide a first stream comprising the first solvent;

(c) a second inlet 306 for receiving a second solution comprising lipid particle-forming materials in a second solvent;

(d) a second inlet microchannel 308 in fluid communication with the second inlet to provide a second stream comprising the lipid particle-forming materials in the second solvent; and (e) a third microchannel 310 for receiving the first and second streams, wherein the third microchannel has a first region 312 adapted for flowing the first and second streams and a second region 314 adapted for mixing the contents of the first and second streams to provide a third stream comprising limit size lipid nanoparticles. The lipid nanoparticles so formed are conducted from the second (mixing) region by microchannel 316 to outlet 318.

In one embodiment, the second region of the microchannel comprises bas-relief structures. In certain embodiments, the second region of the microchannel has a principal flow direction and one or more surfaces having at least one groove or protrusion defined therein, the groove or protrusion having an orientation that forms an angle with the principal direction. In other embodiments, the second region includes a micromixer.

In the devices and systems, means for varying the flow rates of the first and second streams are used to rapidly mix the streams thereby providing the nanoparticles.

In certain embodiments, the devices of the disclosure provide complete mixing occurs in less than 10 ms.

In certain embodiments, one or more regions of the device are heated.

In one embodiment, the first mixer comprises a mixing region comprising a microfluidic mixer configured to mix the first solution and the second solution to provide the nanoparticle solution formed from mixing of the first solution and the second solution.

In one embodiment, the first mixer is a chaotic advection mixer.

In one embodiment, the mixing region comprises a herringbone mixer. While a SHM mixer is illustrated in certain FIGURES (e.g., FIG. 6), it will be appreciated that other mixing configurations are also contemplated. In one embodiment, the mixer is a dean vortexing mixer. In another embodiment, the mixer is a Dean vortex bifurcating mixer (DVBM), which are discussed in greater detail below. In one embodiment, the microfluidic chip includes two different types of chaotic advection mixers. In a further embodiment, the two different types of chaotic advection mixers are SHM and Dean vortexing. In one embodiment, the microfluidic chip includes two different types of chaotic advection mixers, wherein at least one of the two chaotic advection mixers is selected from the group consisting of SHM and Dean vortexing.

In one embodiment, the mixing region has a hydrodynamic diameter of about 20 microns to about 300 microns. In one embodiment, the mixing region has a hydrodynamic diameter of about 113 microns to about 181 microns. In one embodiment, the mixing region has a hydrodynamic diameter of about 150 microns to about 300 microns. As used herein, hydrodynamic diameter is defined using channel width and height dimensions as (2*Width*Height)/(Width+Height).

The mixing region can also be defined using standard width and height measurements. In one embodiment, the mixing region has a width of about 100 to about 500 microns and a height of about 50 to about 200 microns. In one embodiment, the mixing region has a width of about 200 to about 400 microns and a height of about 100 to about 150 microns.

In order to maintain laminar flow and keep the behavior of solutions in the microfluidic devices predictable and the methods repeatable, the systems are designed to support flow at low Reynolds numbers. In one embodiment, the first mixer is sized and configured to mix the first solution and the second solution at a Reynolds number of less than 2000. In one embodiment, the first mixer is sized and configured to mix the first solution and the second solution at a Reynolds number of less than 1000. In one embodiment, the first mixer is sized and configured to mix the first solution and the second solution at a Reynolds number of less than 900. In one embodiment, the first mixer is sized and configured to mix the first solution and the second solution at a Reynolds number of less than 500.

In one embodiment, the microfluidic mixer device contains one micromixer. In one embodiment, the single mixer microfluidic device has two regions: a first region for receiving and flowing at least two streams (e.g., one or more first streams and one or more second streams). The contents of the first and second streams are mixed in the microchannels of the second region, wherein the microchannels of the first and second regions has a hydrodynamic diameter from about 20 to about 500 microns. In a further embodiment, the second region of the microchannel has a principal flow direction and one or more surfaces having at least one groove or protrusion defined therein, the groove or protrusion having an orientation that forms an angle with the principal direction (e.g., a staggered herringbone mixer), as described in US 2004/0262223, expressly incorporated herein by reference in its entirety. In one embodiment, the second region of the microchannel comprises bas-relief structures. In certain embodiments, the second regions each have a fluid flow rate of from 1 to about 50 mL/min. In a preferred embodiment, the mixing channel of the microfluidic device is 300 microns wide and 130 microns high. The herringbone structures are 40 microns high and 50-75 microns thick.

In other embodiments, the first and second streams are mixed with other micromixers. Suitable micromixers include droplet mixers, T-mixers, zigzag mixers, mulitlaminate mixers, or other active mixers.

In one embodiment, microfluidic mixer devices are mounted in a device holder incorporating a clamping system. The device holder and clamping system provides mechanical forces on the microfluidic mixer devices to seal the device inlet and outlet ports. In a further embodiment, the device holder and clamping system comprise sealing gaskets to provide a tight seal between the inlet and outlet ports of the microfluidic mixer device and device holder. In one embodiment, the sealing gasket acts as a spring to evenly distribute forces on the planar microfluidic mixer device when mounted in the device holder by the clamping system. In a preferred embodiment, the sealing gaskets are O-rings. In one embodiment, the device holder and clamping system comprise a solid polycarbonate plate applying mechanical force through tightening screws. In a further embodiment the microfluidic mixer device and device holder are a single disposable plastic piece without the need for a gasket-based clamping system.

Solutions and Products

One function of the systems and methods disclosed herein is to form nanoparticles in solution (the "product"). Previous disclosures by the present inventors relate to generating nanoparticles compatible with the present system, such as those applications previously incorporated by reference. Known and future-developed nanoparticle methods can be performed on the disclosed systems to the extent that the methods require the controlled combination of a first solution with a second solution to form a nanoparticle product, as disclosed herein.

The first solution, also referred to herein as the "aqueous reagent" herein, is provided in a first solution reservoir. In one embodiment, the first solution comprises a first solvent. In one embodiment, the first solution comprises an active pharmaceutical ingredient. In one embodiment, the first solution comprises a nucleic acid in a first solvent. In another embodiment, the first solution comprises a buffer. In one embodiment, the first solution consists essentially of a buffer.

The second solution, also referred to herein as the "solvent reagent" herein, is provided in a second solution reservoir. In one embodiment, the second solution comprises a second solvent. In one embodiment, the second solution comprises lipid particle-forming materials in a second solvent. In one embodiment, the second solvent is a water-miscible solvent (e.g., ethanol or acetonitrile). In certain embodiments, the second solution is an aqueous buffer comprising polymer nanoparticle forming reagents.

In one embodiment, the first solution comprises a nucleic acid in a first solvent and the second solution comprises lipid particle-forming materials in a second solvent.

Parallelization

In the most basic configuration of the disclosed system, a single microfluidic mixer is contained in one microfluidic device on one microfluidic chip. However, increased production volume is achieved by parallelizing the mixers, whether through on-chip parallelization, using multiple chips, or both.

In one embodiment, the system further includes a plurality of mixers, each including a first inlet, a first inlet microchannel, a second inlet, a second inlet microchannel, a mixing microchannel, a mixer outlet, and a chip outlet, wherein the plurality of mixers includes the first mixer. In one embodiment, the plurality of mixers are all of the same dimensions. In another embodiment, the plurality of mixers have different dimensions.

In one embodiment, the plurality of mixers are within a plurality of microfluidic chips. In another embodiment, the plurality of mixers are on a single microfluidic chip.

In one embodiment the microfluidic mixer array incorporates 1-128 microfluidic mixers arrayed in parallel to increase the throughput of the manufacturing system. As an example, a 128-mixer system according to the disclosed embodiments is capable of producing about 1.5 L/min of nanoparticle solution.

Figure 3:
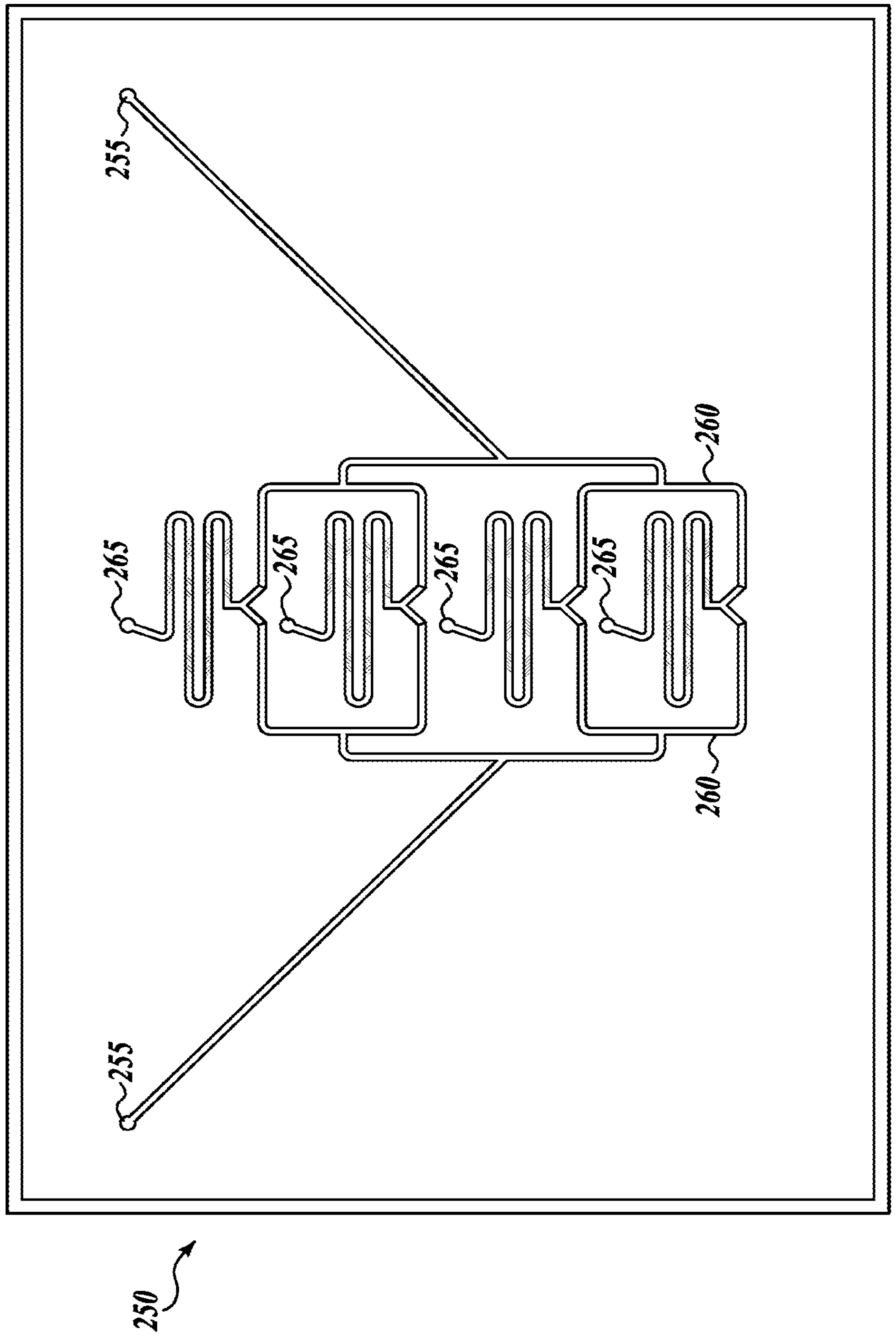
FIG. 3 is a schematic illustration of a representative fluidic device of the disclosure.

In a further embodiment, the microfluidic mixer device contains more than one micromixer. In one embodiment, a single device contains four microfluidic mixers (FIG. 3). In an exemplary embodiment, the microfluidic mixers are arrayed in parallel in a single device. FIG. 3 provides an illustration of a representative device 250, which comprises two inlet channels 255 that feed a fluid manifold system 260 (i.e., an on-chip manifold). The fluid manifold system splits the inlet streams equally among the four microfluidic mixers arrayed in parallel in the single device 260. The output of the microfluidic mixers is collected in the outlets 265. In a further embodiment, the outlet 265 of each mixer is in fluid communication with an outlet manifold system (not pictured) that collects mixed solution from all four devices, in a manner analogous to the outlet manifold 214 of FIG. 2.

The device in FIG. 3 is an example of planar parallelization of microfluidic mixers in a single device. Planar parallelization refers to placing one or more mixers on the same horizontal plane. These mixers may or may not be connected by a fluidic bus channel (e.g., connecting the four outlets 265). Equal flow through each mixer is assured by creating identical fluidic paths between the inlets and outlets. Vertical parallelization is achieved by forming planar mixers and layering them together in such a way as to share common inlets. Theoretically, fluid flowing from the inlets to the lower mixer encounters a higher resistance than that flowing to the top mixer, therefore leading to a lower flow rate. However, by minimizing the separation between mixers, the increased resistance is negligible when compared to the overall resistance of the mixing structure (which is identical for each layer). Additionally, increasing the diameter of the fluidic bus leading to the microfluidic mixer inlets reduces the impendence of the bus and the resulting impedance differences between individual mixers.

In another embodiment, the single device has microfluidic mixers array in the planar and vertical directions of the chip, for high-density 3-dimensional microfluidic parallelization. In other embodiments, microfluidic mixer arrays can be arranged in sequence for multi-step manufacture of complex nanoparticle systems. In certain embodiment, the system of the present disclosure operates at a flow rate between 1 mL/min and 50 mL/min per microfluidic mixer. In another embodiment, at least one microfluidic mixer of the system operates at a flow rate of about 10 mL/min to about 25 mL/min. In a further embodiment each independent continuous flow fluid driver operates at a flow rate of 1.0 L/min.

In one embodiment, at least a portion of the plurality of mixers are parallelized mixers, arranged in parallel, wherein each of the portion of plurality of mixers has a mixer outlet in fluid communication with the system outlet.

In one embodiment, the parallelized mixers are arranged in a stacked configuration on the microfluidic chip.

In one embodiment, the parallelized mixers are arranged in a horizontal configuration, in substantially the same plane, on the microfluidic chip.

In one embodiment, the parallelized mixers are arranged in both a horizontal configuration and a stacked configuration on the microfluidic chip.

In certain embodiments, the disclosure provides devices that include more than one fluidic mixing structures (i.e., an array of fluidic structures). In certain embodiments, the disclosure provides a single device (i.e., an array) that includes from 2 to about 40 parallel fluidic mixing structures capable of producing lipid nanoparticles at a rate of about 2 to about 2000 mL/min. In these embodiments, the devices produce from 100 mL to about 400 L without a change in lipid nanoparticle properties.

In one embodiment, the microfluidic device includes:

(a) a first inlet for receiving a first solution comprising a first solvent;

(b) a first inlet microchannel in fluid communication with the first inlet to provide a first stream comprising the first solvent;

(c) a second inlet for receiving a second solution comprising lipid particle-forming materials in a second solvent;

(d) a second inlet microchannel in fluid communication with the second inlet to provide a second stream comprising the lipid particle-forming materials in the second solvent;

(e) a plurality of microchannels for receiving the first and second streams, wherein each has a first region adapted for flowing the first and second streams and a second region adapted for mixing the contents of the first and second streams to provide a plurality of streams compromising lipid nanoparticles; and (f) a fourth microchannel for receiving and combining the plurality of streams comprising lipid nanoparticle.

In certain embodiments, each of the plurality of microchannels for receiving the first and second streams includes:

(a) a first microchannel in fluidic communication with the first inlet microchannel to receive the first stream comprising the first solvent;

(b) a second microchannel in fluidic communication with the second inlet microchannel to receive the second inlet stream comprising the second solvent; and (c) a third microchannel for receiving the first and second streams, wherein each has a first region adapted for flowing the first and second streams and a second region adapted for mixing the contents of the first and second streams to provide a plurality of streams compromising lipid nanoparticles.

In certain embodiments, the device includes from 2 to about 40 microchannels for receiving the first and second streams. In these embodiments, the device has a total flow rate from 2 to about 1600 mL/min.

In certain embodiments, the second regions each have a hydraulic diameter of from about 20 to about 300 μm. In certain embodiments, the second regions each have a fluid flow rate of from 1 to about 40 mL/min.

For embodiments that include heating elements, the heating element is effective to increase the temperature of the first and second streams in the first and second microchannels to a pre-determined temperature prior to their entering the third microchannel. In these embodiments, the inlet fluids are heated to a desired temperature and mixing occurs sufficiently rapidly such that the fluid temperature does not change appreciably prior to lipid nanoparticle formation.

In one embodiment, the disclosure provides a system for making limit size nanoparticles that includes a parallel microfluidic structure. In a parallel structure, N single mixers are arrayed such that a total flow rate of N×F is achieved, where F is the flow rate used in the non-parallelized implementation. Representative parallel microfluidic structures are illustrated schematically in FIGS. 7-9.

Figure 7:
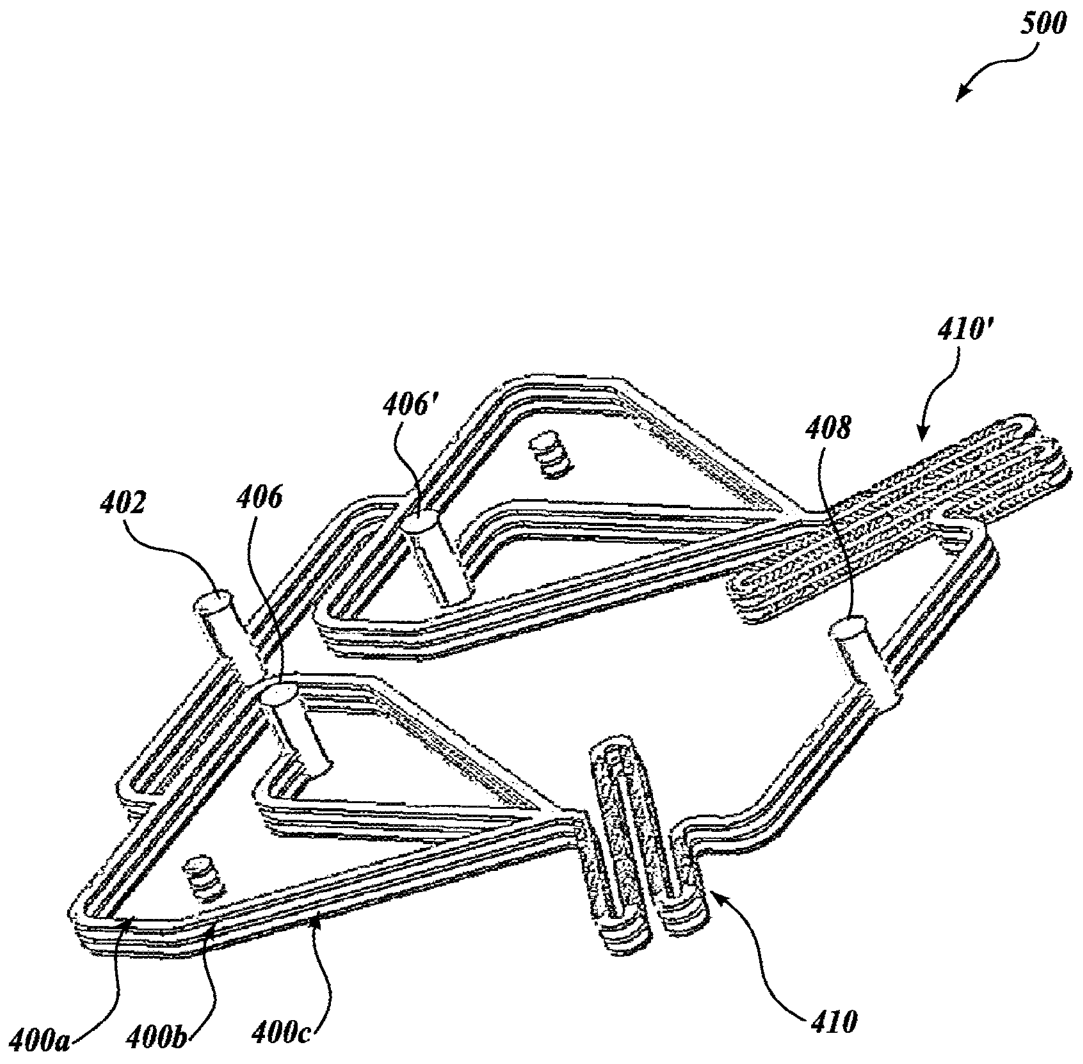
FIG. 7 is a three-dimensional view of a representative parallel fluidic structure useful for making limit size lipid nanoparticles.
Figure 8A:
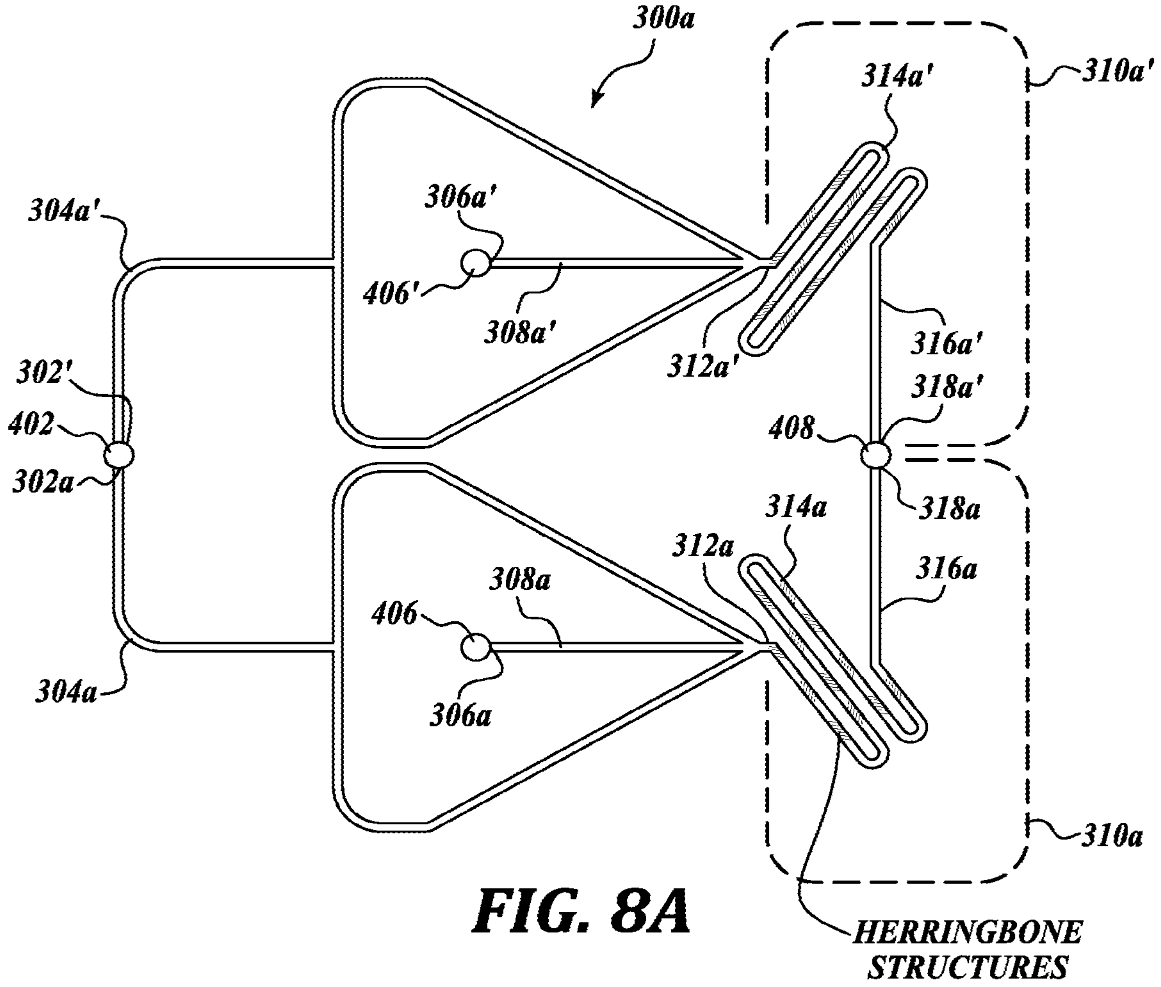
FIG. 8A shows a top view and FIG. 8B shows a side view of the representative parallel fluidic structure shown in FIG. 7. The top view of FIG. 8A shows two planar herringbone structures in parallel. The side view of FIG. 8B shows that the fluidic parallel fluidic structure has three layers, to give a total of six herringbone structures.
Figure 8B:
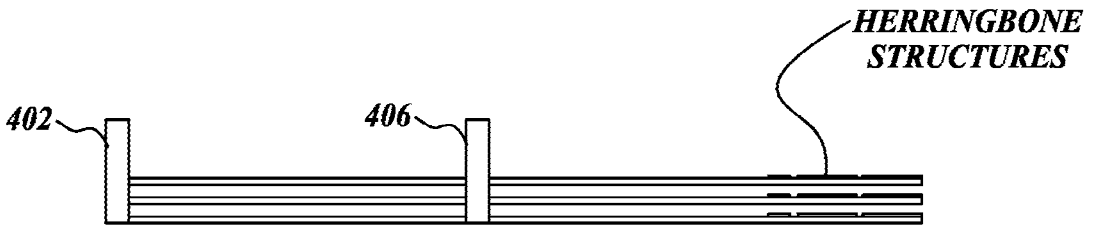

A perspective view of a representative parallel microfluidic structure is illustrated in FIG. 7; a plan view is illustrated in FIG. 8A; and a side elevation view of the device of FIG. 8A is illustrated in FIG. 8B.

Referring to FIG. 7, the device 500 includes three fluidic systems 400_a_, 400_b_, and 400_c_ arranged vertically with each system including one first solvent inlet 402, two second solvent inlets 406 and 406', two mixing regions 410 and 410', and a single outlet 408. Each system includes microchannels for receiving the first and second streams 402 and 406 and 406,' respectively.

Referring to FIGS. 8A and 8B, each fluidic system includes:

(a) a first microchannel 402 in fluidic communication via first inlet 302_a_ with a first inlet microchannel 304_a_ to receive the first stream comprising the first solvent;

(b) a second microchannel 406 in fluidic communication via second inlet 306_a_ with the second inlet microchannel 308_a_ to receive the second inlet stream comprising the second solvent; and (c) a third microchannel 310_a_ for receiving the first and second streams, wherein each has a first region 312_a_ adapted for flowing the first and second streams and a second region 314_a_ adapted for mixing the contents of the first and second streams to provide a plurality of streams comprising lipid nanoparticles. The microchannel 316_a_ conducts one of the plurality of streams from the mixing region to fourth microchannel 408 via outlet 318_a_ that conducts the lipid nanoparticles from the device.

With reference still to FIGS. 8A and 8B, it will be appreciated that in this embodiment of the device, fluidic system 300_a_ includes a second second solvent inlet 406' and mixing region 310_a_' with components denoted by reference numerals 302_a_', 304_a_', 306_a_', 308_a_', 312_a_', 314_a_', 316_a_' and 318_a_'. These reference numerals correspond to their non-primed counterparts 302, 304, 306, 308, 312, 314, 316, and 318 in FIG. 8A and FIG. 8B.

This structure produces vesicles at higher flow rates compared to the single mixer chips and produces vesicles identical to those produced by single mixer chips. In this representative embodiment, six mixers are integrated using three reagent inlets. This is achieved using both planar parallelization and vertical parallelization as shown in FIGS. 7, 8A, and 8B.

Planar parallelization refers to placing one or more mixers on the same horizontal plane. These mixers may or may not be connected by a fluidic bus channel. Equal flow through each mixer is assured by creating identical fluidic paths between the inlets and outlets, or effectively equal flow is achieved by connecting inlets and outlets using a low impedance bus channel as shown in FIG. 9 (a channel having a fluidic impedance significantly lower than that of the mixers).

Figure 9:
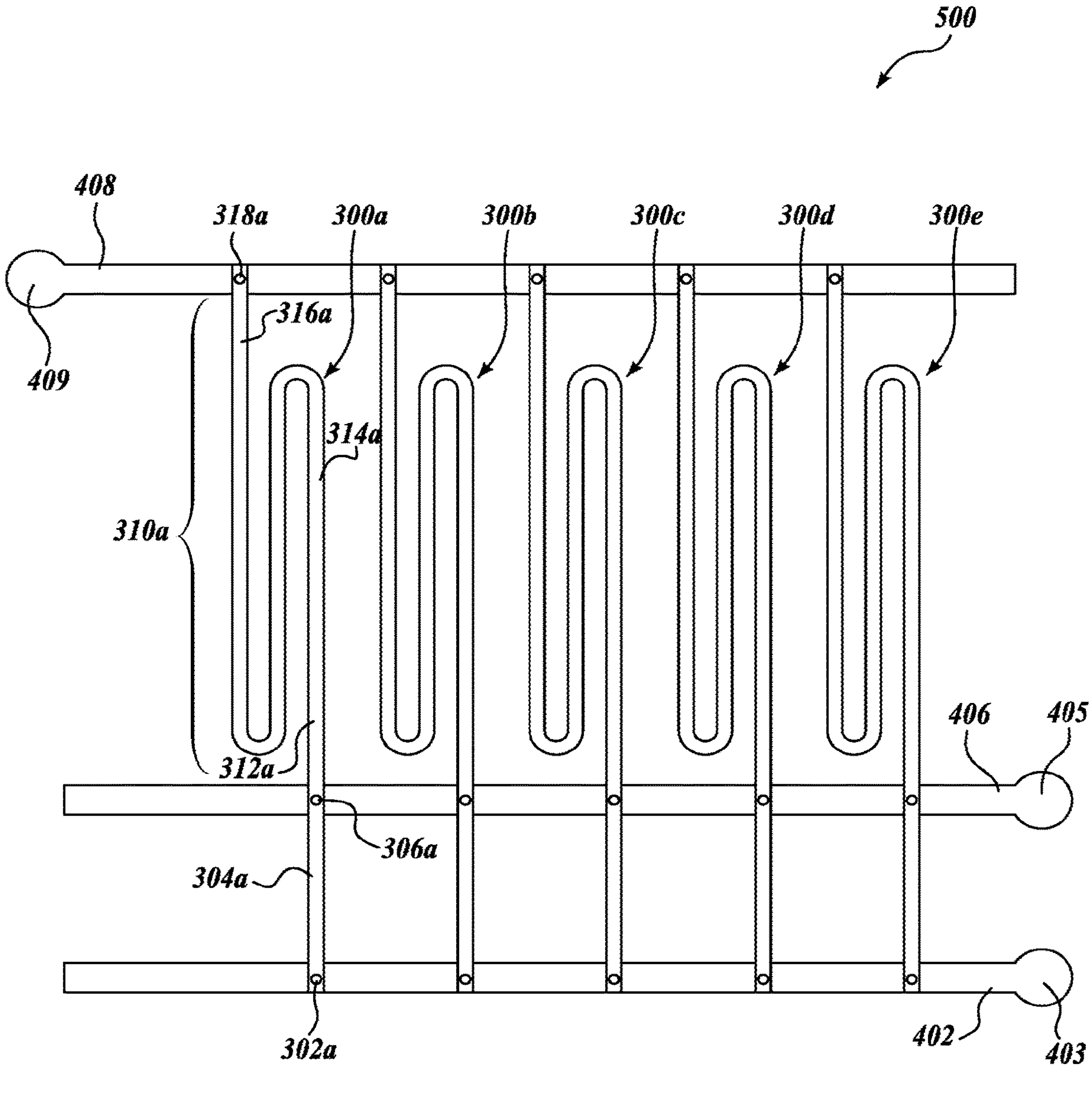
FIG. 9 illustrates a second representative parallel fluidic structure useful for making limit size lipid nanoparticles.

FIG. 9 illustrates a parallelized device 500 includes five fluidic systems 300_a_, 300_b_, 300_c_, 300_d_, and 300_e_ arranged horizontally with each system including one first solvent inlet, one second solvent inlet, one mixing region, and a single outlet 408. Device 500 includes microchannels for receiving the first and second streams 402 and 406 and a microchannel 408 for conducting lipid nanoparticles produced in the device from the device.

Referring to FIG. 9, fluidic system 500_a_ includes:

(a) a first microchannel 402 (with inlet 403) in fluidic communication via first inlet 302_a_ with a first inlet microchannel 304_a_ to receive the first stream comprising the first solvent;

(b) a second microchannel 406 (with inlet 405) in fluidic communication via second inlet 306_a_ with inlet microchannel 304_a_ to receive the second inlet stream comprising the second solvent; and (c) a third microchannel 310*a* for receiving the first and second streams, wherein the third microchannel has a first region 312*a* adapted for flowing the first and second streams and a second region 314*a* adapted for mixing the contents of the first and second streams to provide a third stream compromising lipid nanoparticles. In FIG. 9, microchannel 316*a* conducts the third stream from the mixing region to fourth microchannel 408 via outlet 318*a*. Microchannel 408 conducts the lipid nanoparticles from the device via outlet 409.

Figure 6:
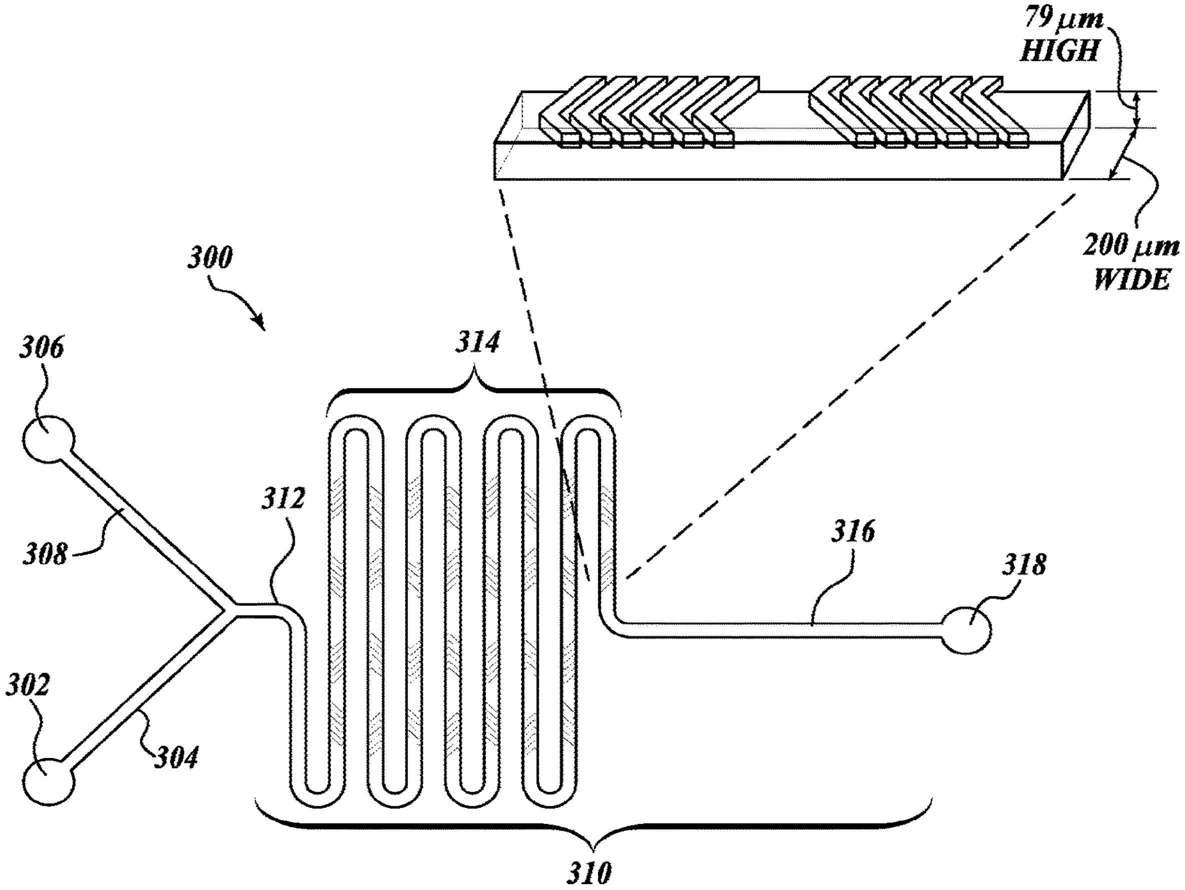
FIG. 6 is a schematic illustration of a representative system of the disclosure, a continuous-flow staggered herringbone (SHM) micromixer. The mixing of two separate streams occurs in the patterned central channel which grooved walls drive alternating secondary flows that chaotically stir the fluids injected. The chaotic mixing leads to exponential increase of the interfacial area thus reducing the diffusion distances between two fluids. Rapid interdiffusion of the two phases (aqueous and ethanolic containing fully solvated lipids) results in the self-assembly of LNPs, whose size depends primarily on their lipid composition and aqueous/ethanolic flow rate ratio.

In the fluidic system of FIG. 9, the five fluidic systems 300*a*-300*e* are arranged in a single plane that is not the plane of the first microchannel 402, second microchannel 406, or fourth microchannel 408. Therefore, the fluidic busses (embodied by 402, 406, and 408) are in one plane and the mixers (embodied by 300*a*-300*e*) are in a separate plane. While this configuration adds an additional layer of fabrication complexity to the device (e.g., by requiring an additional layer of lithography to define the layer with the mixers), such a parallelized device provides dramatically enhanced throughput without a proportional amount of device area required. For example, in the device of FIG. 9, the footprint of the device 500 on a chip is much less than the combined footprints of five individual devices with comparable total mixed-volume output. Accordingly, in one embodiment, the parallelized device has n fluidic systems (e.g., 300*a* et al.) and is configured to produce a mixed output volume that is the same or greater than the output of n standalone mixers (e.g., as illustrated in FIG. 6), and in a smaller total device area (i.e., the parallelized device has a device area that is less than the total combined area of the n standalone mixers.

With reference to FIGS. 8A and 8B, it will be appreciated that in this embodiment of the device, fluidic system 300*a* includes a second second solvent inlet 406' and mixing region 310*a*' with components denoted by reference numerals 302*a*', 304*a*', 306*a*', 308*a*', 312*a*', 314*a*', 316*a*' and 318*a*'. These reference numerals correspond to their non-primed counterparts 302, 304, 306, 308, 312, 314, 316, and 318 in FIG. 8A and FIG. 8B.

In one embodiment, the disclosure provides a device for producing limit size lipid nanoparticles, comprising n fluidic devices, each fluidic device comprising:

(a) a first inlet 302*a* for receiving a first solution comprising a first solvent;

(b) a first inlet microchannel 304*a* in fluid communication with the first inlet to provide a first stream comprising the first solvent;

(c) a second inlet 306*a* for receiving a second solution comprising lipid particle-forming materials in a second solvent;

(d) a third microchannel 310*a* for receiving the first and second streams, wherein the third microchannel has a first region 312*a* adapted for flowing the first and second streams and a second region 314*a* adapted for mixing the contents of the first and second streams to provide a third stream comprising limit size lipid nanoparticles conducted from the mixing region by microchannel 316*a*, wherein the first inlets 302*a*-302*n* of each fluidic device 300*a*-100*n* are in liquid communication through a first bus channel 402 that provides the first solution to each of the first inlets, wherein the second inlets 306*a*-306*n* of each fluidic device 300*a*-300*n* are in liquid communication through a second bus channel 406 that provides the second solution to each of the second inlets, and wherein the outlets 318*a*-318*n* of each fluidic device 300*a*-300*n* are in liquid communication through a third bus channel 408 that conducts the third stream from the device. The reference numerals refer to representative device 500 in FIG. 9.

In certain embodiments, n is an integer from 2 to 40.

Vertical parallelization is achieved by forming planar mixers and stacking them together and connecting the inlets and outlets through a vertical bus. Theoretically, fluid flowing from the inlets to the lower mixer encounters a higher resistance than that flowing to the top mixer, therefore leading to a lower flow rate. However, as the distance separating the two mixers is less than 500 microns, the increased resistance is negligible when compared to the overall resistance of the mixing structure (which is identical for each layer). This is confirmed both through the experimental results and through fluid flow simulations. The distance separating mixing layers for which this condition is true is dependent on the width of the bus.

Parallelized devices are formed by first creating positive molds of planar parallelized mixers that have one or more microfluidic mixers connected in parallel by a planar bus channel. These molds are then used to cast, emboss or otherwise form layers of planar parallelized mixers, one of more layers of which can then be stacked, bonded and connected using a vertical bus channels. In certain implementations, planar mixers and buses may be formed from two separate molds prior to stacking vertically (if desired). In one embodiment positive molds of the 2× planar structure on a silicon wafer are created using standard lithography. In an exemplary manufacturing method, a thick layer of on-ratio PDMS is then poured over the mold, degassed, and cured at 80° C. for 25 minutes. The cured PDMS is then peeled off, and then a second layer of 10:1 PDMS is spun on the wafer at 500 rpm for 60 seconds and then baked at 80° C. for 25 minutes. After baking, both layers are exposed to oxygen plasma and then aligned. The aligned chips are then baked at 80° C. for 15 minutes. This process is then repeated to form the desired number of layers. Alignment can be facilitated by dicing the chips and aligning each individually and also by making individual wafers for each layer which account for the shrinkage of the polymer during curing.

Using a custom chip holder, this chip has been interfaced to pumps using standard threaded connectors. This has allowed flow rates as high as 72 ml/min to be achieved. Previously, in single element mixers, flows about 10 ml/min were unreliable as often pins would leak eject from the chip. In order to interface with these holders, chips are sealed to on the back side to glass, and the top side to a custom cut piece of polycarbonate or glass with the interface holes pre-drilled. The PC to PDMS bond is achieved using a silane treatment. The hard surface is required to form a reliable seal with the O-rings. A glass backing is maintained for sealing the mixers as the silane chemistry has been shown to affect the formation of the nanoparticles.

The devices and systems of the disclosure provide for the scalable production of limit size nanoparticles. The following results demonstrate the ability to produce identical vesicles, as suggested by identical mean diameter, using the microfluidic mixer illustrated in FIGS. 7-8B.

Manifolds

In one embodiment, the present disclosure includes a manifold system that splits the fluid streams from the two, or more independent continuous flow pumping systems into multiple fluid streams and directs the multiple fluid streams into a microfluidic mixer array. In another embodiment, a single device contains multiple microfluidic mixers with on-device or off-device fluid distribution scheme, such as, but not limited to a fluid bus.

As used herein, the term "manifold" is referred to as any fluid conduit that splits or merges liquid flow. A manifold can be external to a microfluidic device (e.g., interfaced with a microfluidic chip via an inlet or outlet port, such as illustrated in FIG. 10) or integrated into the microfluidic chip, as illustrated in FIG. 3.

In one embodiment, illustrated in FIG. 2, fluid flow driven by the independent continuous flow pumping systems enters two manifolds, a first manifold 210 connected to the aqueous fluid driver 208 and a second manifold 211 connected to the solvent fluid driver 206. The manifolds 210 and 211 split the solutions flowing therein into multiple fluid streams that flow to parallelized microfluidic mixing devices 212.

In another embodiment, a third manifold 214 is used to collect the multiple streams emerging from the microfluidic mixer array into a single output stream. In one embodiment, the 8 separate fluid streams containing nanoparticles emerging from the microfluidic mixer array consisting of 8 parallelized microfluidic mixer devices containing a single microfluidic mixer are merged through a manifold to form a single output stream.

In one embodiment, the system further comprises a first manifold configured to receive the first solution from the first solution reservoir and distribute the first solution to the first inlets of the plurality of mixers.

In one embodiment, the system further includes a second manifold configured to receive the second solution from the second solution reservoir and distribute the second solution to the second inlets of the plurality of mixers.

In one embodiment, the system further comprises a third manifold configured to receive and combine the nanoparticle solution from the chip outlets of the plurality of mixers and direct it in a single channel towards the system outlet.

In one embodiment, the system further comprises:

- a first manifold configured to receive the first solution from the first solution reservoir and distribute the first solution to the first inlets of the plurality of mixers;
- a second manifold configured to receive the second solution from the second solution reservoir and distribute the second solution to the second inlets of the plurality of mixers; and
- a third manifold configured to receive and combine the nanoparticle solution from the chip outlets of the plurality of mixers and direct it in a single channel towards the system outlet.

In one embodiment, the plurality of mixers are within the microfluidic chip.

Representative manifold materials include PEEK, stainless steel, COC/COP, polycarbonate, and Ultem.

In one embodiment, the manifold device comprises, but not limited to, 9-Ports interfaced with 0.0625 inch outside diameter tubing. In another embodiment, the interface between the 0.0625 inch outside diameter tubing and ports of the manifold are made using 10-24 threaded fittings in the form of a single piece. In another embodiment, the interface between the 0.0625 inch outside diameter tubing and ports of the manifold are made using 10-24 threaded fittings as a nut and ferrule. In another embodiment, a 9-Port 0.0625 inch outside diameter tubing manifold is used to split fluid flow driven by the independent continuous flow pumping systems into 8 separate fluid streams that feed into 8 parallelized microfluidic mixer devices containing a single microfluidic mixer. The relative flow rates of the multiple output streams generated by the manifold are governed by the relative fluidic resistance of each output stream. In a parallelized microfluidic mixer array, the microfluidic mixer provides over 95% of the fluidic resistance in the fluid path. Thus, the equal distribution of flow is attributed to the microchannel features in the microfluidic mixer device and the relative difference in tubing length, from the manifold to microfluidic mixer device, is insignificant.

Fluid Driver Systems

In one embodiment, the fluid drivers are pumps. In one embodiment, the system includes two, or more, independent continuous flow fluid drivers.

In the embodiment illustrated in FIG. 2, the solvent metering pump 206 and aqueous metering pump 208 are independent continuous flow pumping systems that provide fluid flow in the apparatus.

In one embodiment, the first continuous flow fluid driver and the second continuous flow fluid driver are independently selected from the group consisting of positive displacement fluid drivers (such as: reciprocating piston, peristaltic, gear, diaphragm, screw, progressive cavity); centrifugal pumps; and pressure driven pumps In one embodiment, the continuous flow pumping systems are positive displacement pumps. Examples of positive displacement pumps include, but are not limited to, peristaltic pumps, gear pumps, screw pumps, and progressive cavity pumps. In a preferred embodiment, the independent continuous flow pumps are dual head reciprocating positive displacement pumps.

In another embodiment the dual head reciprocating positive displacement pumps have front mounted interchangeable pump heads. In a further embodiment the front mounted interchangeable pump heads enable independent flow rates from 10 mL/min to 1000 mL/min.

In another embodiment, the dual head reciprocating positive displacement pumps are Knauer Azura P2.2 L pumps. In a further embodiment the Knauer Azura P 2.1 L pumps are modified to have the pressure sensor mounts external to the pump body allowing easy exchange of the pump's pressure sensor.

Interchangeable pump heads enable simple and rapid scaling of continuous flow manufacturing system. In certain embodiments, the front mounted interchangeable pump heads control the ratio of fluid flow rate from the aqueous reservoir 204 to fluid flow rate from the solvent reservoir 202. In certain embodiments, the ratio of the flow rate from the aqueous reservoir 204 to the flow rate from the solvent reservoir 202 is greater than 1:1 (e.g., 2:1, 3:1, 4:1, 5:1, 6:1, 7:1, 8:1, 9:1, 10:1, including intermediate ratios). In other embodiments, the ratio of the flow rate from the solvent reservoir 102 to the flow rate from the aqueous reservoir 204 is greater than 1:1 (e.g., 2:1, 3:1, 4:1, 5:1, 6:1, 7:1, 8:1, 9:1, 10:1, including intermediate ratios). FIG. 10 illustrates a system operating with a ratio of 3:1 (Pump #2:Pump #1).

In one embodiment, the dual head reciprocating pump head provides low pulsation flow. In a further embodiment, the pulsation is further dampened through the addition of 10-500 PSI backpressure. Preferred embodiments of backpressure systems include, but are not limited to, a backpressure regulator, or tubing of extended length, added to the outlet of the pumping systems. In one embodiment, backpressure is achieved by addition of 24 inches of tubing with an internal diameter of 0.02 inches.

In another embodiment, independent continuous flow pumping systems are chosen from centrifugal pumps, and pressure driven pumps. The independent continuous flow pumping system provides easy interchange of components and reduces the time needed to replace single-use fluid contacting components.

Dilution

In one embodiment, the system further includes a dilution element, wherein the dilution element comprises a third continuous flow fluid driver, configured to continuously drive a dilution solution from a dilution solution reservoir into the system, via a dilution channel, in between the chip outlet and the system outlet.

In a further embodiment, referring to FIG. 2, the present disclosure includes one or more additional pumps 218 to dilute the nanoparticles emerging from the microfluidic mixer array with a buffer 216), or other suitable media. In certain embodiments, the dilution process is achieved by pumping one or more buffers continuously into the output stream emerging from the microfluidic mixer array. In one embodiment, the dilution pumping system is a positive displacement pump. In a further embodiment the positive displacement pump is selected from peristaltic pumps, gear pumps, screw pumps and progressive cavity pumps. In certain embodiments the dilution pumping system is a peristaltic pump. In certain embodiments the dilution pumping system is a peristaltic pump with dual pump heads. In a preferred embodiment, the dilution pumping system is a Masterflex peristaltic pump with dual pump heads. In another embodiment the pumping system is selected from centrifugal pumps and pressure driven pumps. The choice of pumps listed here is representative and should not limit the scope of the present disclosure. A person of ordinary skill will recognize other alternative pumping systems that may be used with the present disclosure.

In certain embodiments, the dilution media is introduced into the nanoparticle stream by a connector. In one embodiment the connector is a Tee connector. In another embodiment the connector is a Y-connector. In certain embodiments, the dilution media contacts the nanoparticle stream at an angle ranging from 0.1° to 179.9°. The angle of contact moderates the level of agitation induced onto the nanoparticles in the dilution process. In a preferred embodiment, the Masterflex peristaltic pump dual pump heads have roller profiles offset by 30° thereby reducing the pump's output flow pulsation level by 80-95%.

In certain embodiments, the dilution media is introduced into a second, inline microfluidic mixer. In one embodiment, the second microfluidic mixer is on a second, inline device. In another embodiment, the second microfluidic mixer is on the same microfluidic device.

Diluting the nanoparticle solution reduces the percentage of solvent present in the solution. For certain nanoparticles, diluting the solvent below 50% increases particle stability. In other embodiments, nanoparticle stability is promoted by diluting solvent below 25%. In further embodiments, nanoparticles are stable below 10% solvent content.

In apparatus 200 (FIG. 2), there are two reservoirs, solvent reservoir 202 and aqueous reservoir 204. In one embodiment the reservoirs are disposable bags. In a further embodiment, the reservoirs are vessels, including, but not limited to, stainless steel reservoirs. In one embodiment, the solvent is a water-miscible solvent such as, but not limited to, ethanol containing one or more lipids, and the aqueous is a low pH buffer such as, but not limited to, citrate buffer pH 4.0. In a further embodiment the low pH buffer such as, but not limited to, citrate buffer pH 4.0 contains one or more nucleic acids. In a further embodiment, the solvent is a water-miscible solvent such as, but not limited to, acetonitrile containing one or more polymers, or polymer-drug conjugates and the aqueous is a buffer such as, but not limited to, citrate buffer pH 4.0. For the formation of polymer nanoparticles, a representative buffer is a saline solution.

In one embodiment the tubing 226 is a microfluidic channel on the microfluidic chip. In one embodiment the tubing 226 is metal tubing external to the microfluidic chip. In an embodiment the tubing is plastic tubing. In another embodiment the internal diameters of the tubing ranges from 0.01 inches to 0.25 inches. In another embodiment the fittings 220, 222 include, but are not limited to, barbed, compression, sanitary and threaded. In a further embodiment the fittings are metal or plastic. In a preferred embodiment the fittings are plastic.

In one embodiment the manufacturing apparatus has a mechanism to dilute the nanoparticle fluid stream emerging from the microfluidic mixer array. In one embodiment dilution is achieved by in-line dilution where the aqueous buffer contacts directly with the output stream.

In one embodiment a fluid driver 218 flows dilution reagent from a reservoir 216 and the dilution reagent stream joins the nanoparticle fluid stream at a junction where flow of dilution reagent stream is controlled by a tee connector 220. In another embodiment a fluid driver 218 flows dilution reagent from a reservoir 216 and the dilution reagent stream enters a microfluidic mixer device through one inlet and the nanoparticle fluid stream enters the microfluidic mixer device through a second inlet and the two streams flow into a microfluidic mixer region where the nanoparticle fluid stream is diluted by mixing with the dilution reagent fluid stream. In further embodiment a fluid driver 218 flows dilution reagent from a reservoir 216 and the dilution reagent fluid stream enters a manifold where the dilution reagent fluid stream is divided into multiple dilution reagent fluid streams and the nanoparticle fluid stream enters a manifold where the nanoparticle fluid stream is divided into multiple nanoparticle fluid streams. The multiple dilution reagent fluid streams and the multiple nanoparticle fluid streams enter multiple microfluidic mixer devices arrayed in parallel where the nanoparticle fluid stream is diluted by mixing with the dilution reagent fluid stream. In one embodiment the ratio of flow rate of the nanoparticle fluid stream to the flow rate of the dilution reagent fluid stream is greater than 1:1 (e.g., 2:1, 3:1, 4:1, 5:1, 6:1, 7:1, 8:1, 9:1, 10:1, including intermediate ratios). In other embodiments, the ratio of flow rate of the dilution reagent fluid stream to the flow rate of the nanoparticle fluid stream greater than 1:1 (e.g., 2:1, 3:1, 4:1, 5:1, 6:1, 7:1, 8:1, 9:1, 10:1, including intermediate ratios).

In one embodiment, the system includes dilution in-line in the absence of the microfluidic device.

Waste Valve

In a further embodiment of the present disclosure, the microfluidic-based continuous flow manufacturing apparatus for scalable production of nanoparticles includes a mechanism to separate waste collection 224 from sample collection 228 as shown in FIG. 2. In one embodiment, a valving system directs the output stream to waste collection or sample collection. In one embodiment, a two-vessel collection (waste and sample) is achieved by splitting the output stream from the manufacturing system into two and opening/closing valves on the independent lines to collect in the desired vessel. In one embodiment the valve system is a manual system or an automated system is used to pinch off the soft tubing. In a further embodiment the manual valve system is a tube clamp. In a further embodiment the automated system is a solenoid pinch valve.

In one embodiment, the system further includes a waste outlet in fluid communication with a waste valve in between the chip outlet and the system outlet, wherein the waste valve is configured to controllably direct fluid towards the waste outlet. The waste valve is used to eliminate waste from priming the system or other non-production operations. As illustrated in FIG. 2, the waste valve 222 directs flow to a waste vessel 224 that is separate from the sample vessel 228.

Fully Disposable Fluid Path

In one embodiment of the present disclosure, the system incorporates a fully disposable fluid path. As used herein, the term "disposable fluid path" refers to a system where every element that touches a liquid is "disposable." Given the precious nature of certain products of the system (e.g., nano-medicines), and the related value of such products, the term "disposable" as used herein refers to a component that has relatively low cost in relation to the product produced. Typical disposable components include tubing, manifolds, and reservoirs that may be made of plastic. However, in the present disclosure, disposable also refers to such components as pump heads and microfluidic chips. Therefore, disposable components include those that are made from metal (e.g., pump heads) and/or are finely manufactured (e.g., microfluidic devices).

In the embodiment illustrated in FIG. 2, the fully disposable fluid path includes the reagent bags 202, 204, 216), the tubing 226), the interchangeable pump heads 206, 208), the fittings 220, 222), the manifolds 210, 211 214), and the microfluidic devices 212.

In one embodiment, the disposable fluidic path includes a disposable microfluidic chip, a disposable first pump head of the first continuous flow pump, a disposable second pump head of the second continuous flow pump, and a disposable system outlet.

In one embodiment, the disposable first pump head and the disposable second pump head are made of a material independently selected from the group consisting of stainless steel, polymers (e.g., polyetheretherketone (PEEK)), titanium, and ceramic. In one embodiment, at least one of the disposable first pump head or the disposable second pump head comprise a metal.

In one embodiment, every surface touched by the first solution, the second solution, and the nanoparticle solution are disposable.

In certain embodiments the apparatus fluid path is fully disposable. In certain embodiments the apparatus is GMP compliant. All fluid contacting materials in these embodiments can be reused, or be single-use disposable.

Sterile System Components

In one embodiment, the microfluidic chip is sterile. Sterilization is essential for certain production processes. In a further embodiment, the microfluidic chip is sterilized prior to integration into the system. In another embodiment, the microfluidic chip is sterilized in-place within the system.

Representative sterilization methods include steam autoclave, dry heat, chemical sterilization (i.e., sodium hydroxide or ethylene oxide), gamma radiation, gas, and combinations thereof. In a specific embodiment, the microfluidic chip is sterilized with gamma radiation.

Due to the importance of sterilization in certain applications, in certain embodiments the microfluidic chip is formed from materials that are compatible with certain types of sterilization preferred for a particular application.

In one embodiment, the microfluidic chip is formed from materials that are compatible with gamma radiation. Materials compatible with gamma radiation are those that can be irradiated. For example, polycarbonate, cyclic olefin polymer, cyclic olefin copolymer, and high- and low-density polyethylene. Materials that cannot be irradiated include polyamides, polytetrafluoroethylene, and any metal.

In addition to providing embodiments that facilitate sterilization of system components, further embodiments include sterile packages containing sterile systems and/or system parts. These sterile packages allow a user to reduce time and cost by avoiding in-place sterilization procedures.

Additionally, certain particles that can be synthesized using the disclosed systems are incompatible with terminal sterilization and therefore cannot be sterilized downstream—therefore, a sterile manufacturing path is required. Generally, sterile filtering is a technique used for terminal sterilization and particles having a dimension (e.g., diameter) greater than about 200 nm are not compatible with terminal sterilization. Accordingly, in one embodiment, the systems and methods are configured to provide sterile synthesis of particles having a dimension of 200 nm or greater. Accordingly, in one embodiment, the systems and methods are configured to provide sterile synthesis of particles without terminal sterilization.

Representative particles that are not compatible with terminal sterilization (e.g., sterile filtering) include DNA/RNA lipoplexes manufactured by mixing DNA/RNA with pre-formed liposomes, which can result in particle structures that are larger than 200 nm, which cannot be terminally sterilized. Certain drug-conjugated polymer nanoparticles with high polydispersity are also large enough to make terminal sterilization impractical.

According to the disclosed embodiments, a sterile package can be opened in the production environment, the contents of the package implemented into the system, and the system operated without a pre-sterilization step. Accordingly, in one embodiment, sterile package is provided. In one embodiment, the sterile package includes a sterile microfluidic chip according to the present disclosure sealed within the sterile package. In a further embodiment, the sterile package includes an entire sterile disposable fluidic path, including pump heads, sealed within the sterile package.

The sterile system parts can be sterilized by any methods know to those of skill in the art and disclosed herein. For example, gamma radiation is used in certain embodiments to sterilize the system parts.

After sterilization, the sterile system parts are maintained in a sterile environment and packaged in a sealed manner so as to maintain sterility until use.

In certain embodiments nanoparticle manufacturing is conducted in a specialized barrier facility that eliminates the requirement for filtration to ensure a sterile product.

Software Control

In the system is controlled by software (e.g., FIG. 1 part 102). In further embodiments the entire manufacturing system is software controlled. Such software controls are generally known to those of skill in the art. In one embodiment, with reference to FIG. 2, software controls the first 202 and second 204 fluid drivers. In a further embodiment, software controls all fluid drivers in the system 100 or 200.

Methods for Making Nanoparticles

In one embodiment the present disclosure provides methods for scalable production of nanoparticles using the microfluidic-based continuous flow manufacturing apparatus of the disclosure.

In one aspect, a method of forming nanoparticles is provided. In one embodiment, the method comprises flowing a first solution and a second solution through a system according to any of the disclosed embodiment and forming a nanoparticle solution in the first mixer of the microfluidic chip.

In one embodiment, the system comprises a plurality of mixers and the method further comprises flowing the first solution and the second solution through the plurality of mixers to form the nanoparticle solution, wherein the plurality of mixers includes the first mixer.

In one embodiment, the plurality of mixers are contained within a plurality of microfluidic chips.

In one embodiment, the plurality of mixers are contained within a single microfluidic chip.

In one embodiment, the apparatus provides a system and process for the manufacture of lipid nanoparticles containing a therapeutic material.

In another embodiment the apparatus provides a system and process for the manufacture of polymer nanoparticles containing a therapeutic material.

In one embodiment the apparatus has two reservoirs: a solvent reservoir and aqueous reservoir. In one aspect, the solvent reservoir contains a water-miscible solvent such as, but not limited to, ethanol containing one or more lipids. In another aspect, the solvent reservoir contains a water-miscible solvent such as, but not limited to, acetonitrile containing one or more polymers, or polymer-drug conjugates. In one aspect, the aqueous reservoir contains a buffer such as, but not limited to, citrate buffer pH 4.0. In a further aspect, the aqueous reservoir contains a buffer such as, but not limited to, citrate buffer pH 4.0 that contains one or more therapeutic materials.

In one embodiment, the contents of the reservoirs are drawn into the fluid path of the apparatus of the disclosure by independent continuous flow pumping systems. In one aspect the each independent continuous flow manufacturing pump operates at a flow rate of 0.1 L/min-1.0 L/min. In one aspect, the present disclosure includes a manifold system that splits the fluid streams from the two, or more independent continuous flow pumping systems into multiple fluid streams such that:

(a) a first stream comprising a first solvent (e.g., an aqueous buffer) is introduced into the first channel of each independent microfluidic mixer at a first flow rate;

(b) a second stream comprising a second solvent (e.g., an water-miscible solvent) into the second channel of each independent microfluidic mixer at a second flow rate to provide first and second adjacent streams, wherein the first and second solvents are not the same, and wherein the ratio of the first flow rate to the second flow rate is greater than 1.0;

(c) flowing the first and second streams from the first region to the second region; and (d) mixing the first and second streams in the second region of the apparatus to provide a third stream comprising lipid nanoparticles.

In one embodiment, the apparatus is a microfluidic apparatus. In certain embodiments, the flow pre-mixing is laminar flow. In certain embodiment, mixing the first and second streams comprises chaotic advection. In other embodiments, mixing the first and second streams comprises mixing with a micromixer.

In one aspect the microfluidic mixer array incorporates 1-128 microfluidic mixers arrayed in parallel to increase the throughput of the manufacturing system. In certain aspects a single microfluidic mixer is contained on one device. In another aspect, a single device contains multiple microfluidic mixers. In one embodiment, a single device contains four microfluidic mixers (FIG. 3).

In one embodiment, the flow rates of the first stream and second stream flow rate between 1 mL/min and 50 mL/min per microfluidic mixer.

In certain embodiments the ratio of the first flow rate to the second flow rate is greater than 1:1 (e.g., 2:1, 3:1, 4:1, 5:1, 6:1, 7:1, 8:1, 9:1, including intermediate ratios).

In certain embodiments the final nanoparticle product is dispensed into sterile vials.

Dean Vortex Bifurcating Mixers ("DVBM")

As noted above, DVBM are useful as mixers in the disclosed continuous flow systems. DVBMs of the type disclosed herein act as efficient mixers and whose injection molding tooling can be produced by an end mill with a radius of R (for example 300 μm). The provided DVBM mixers include a plurality of toroidal mixing elements (also referred to herein as "toroidal mixers." As used herein, "toroid" refers to a generally circular structure having two "leg" channels that define a circumference of the toroid between an inlet and an outlet of the toroidal mixer. The toroidal mixers are circular in certain embodiments. In other embodiments, the toroidal mixers are not perfectly circular and may instead have oval or non-regular shape.

Figure 12A:
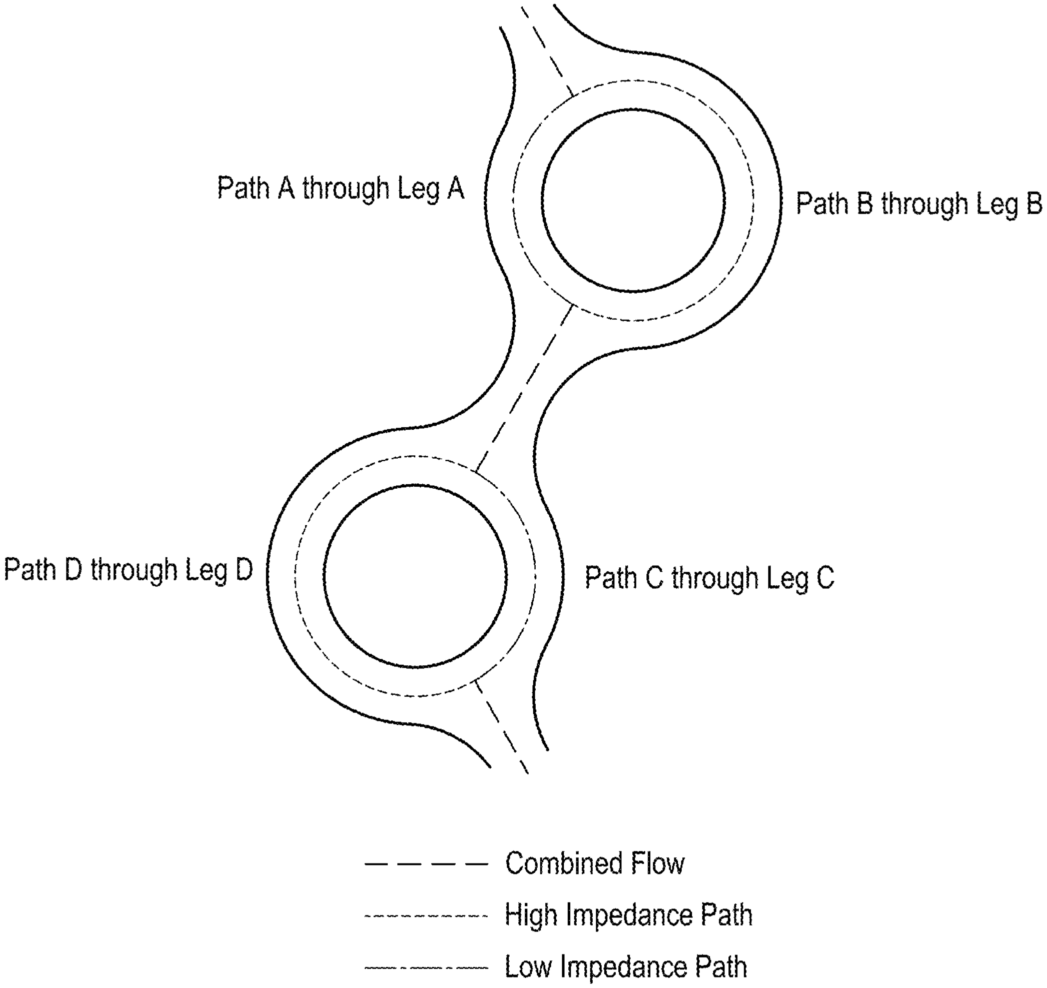
FIG. 12A illustrates a toroidal pair Dean vortex bifurcating mixers (DVBM) in accordance with the disclosed embodiments.
Figure 12B:
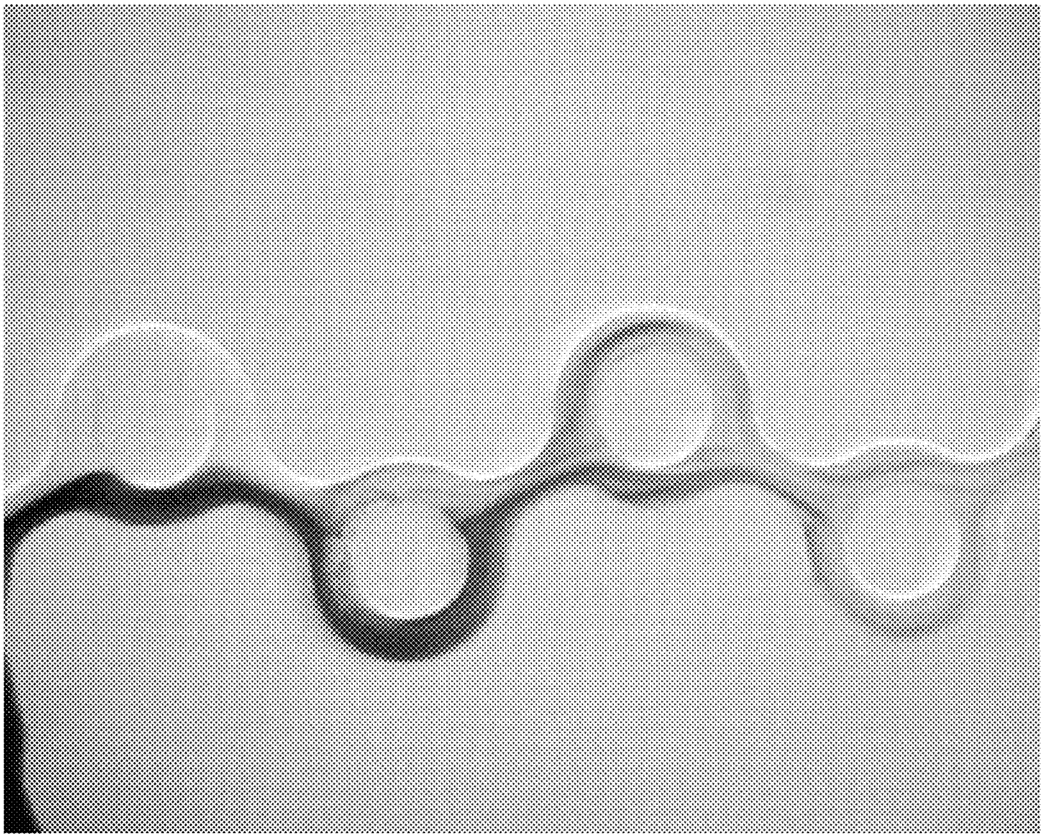
FIG. 12B is a photograph of an exemplary toroidal DVBM mixer in accordance with the disclosed embodiments.
Figure 13:
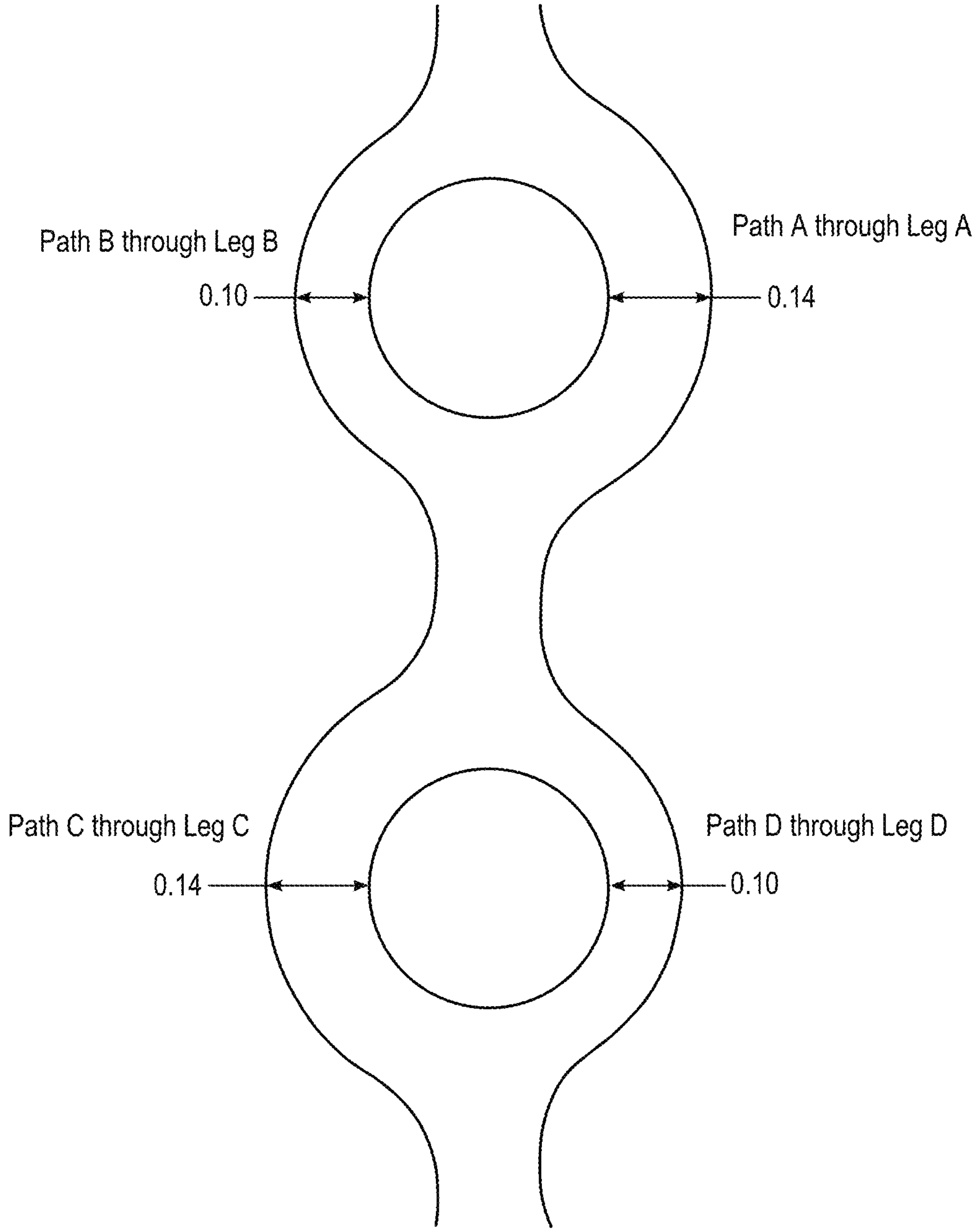
FIGS. 13 and 14 are diagrammatic illustrations of portions of DVBM mixers in accordance with embodiments disclosed herein.
Figure 14:
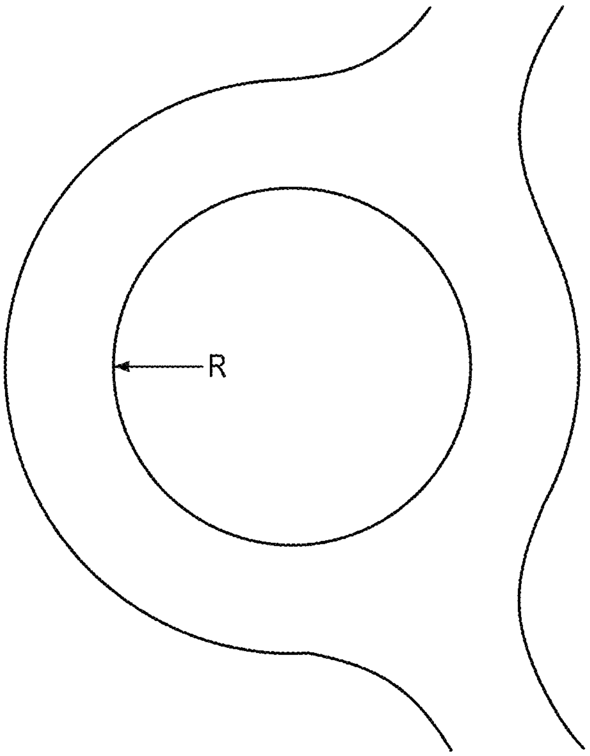
Figure 15:
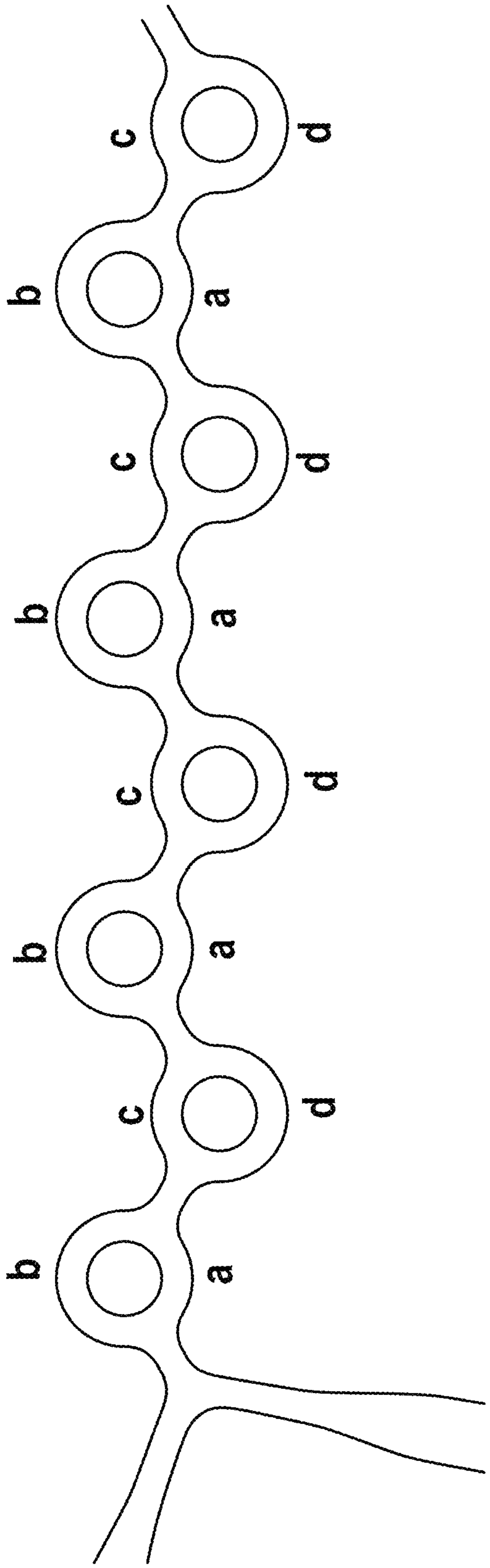
FIG. 15 is an illustration of an exemplary DVBM mixer in accordance with embodiments disclosed herein.
Figure 16:
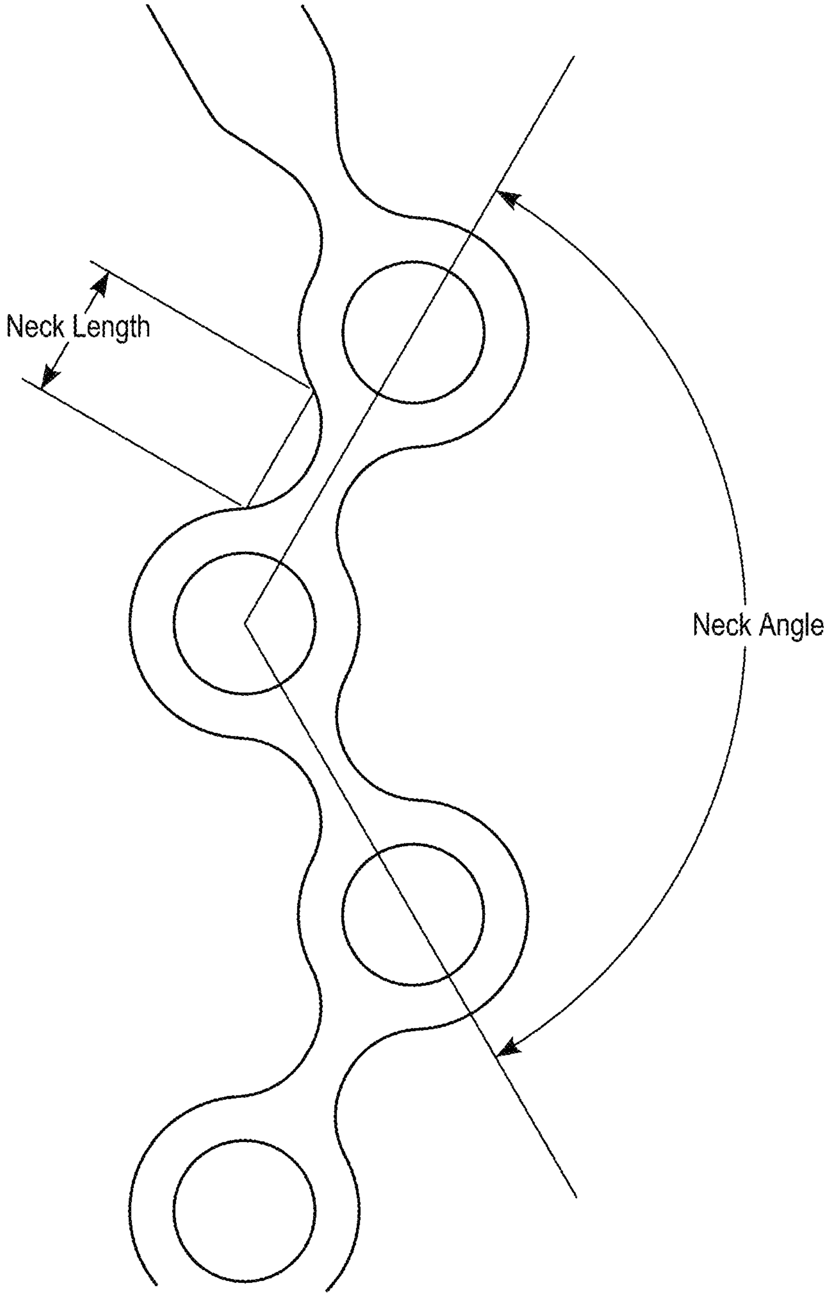
FIG. 16 is a diagrammatic illustration of a portion of a DVBM mixer in accordance with embodiments disclosed herein.

FIG. 12A illustrates a pair of toroidal DVBM mixers in accordance with the disclosed embodiments. FIG. 12B is a photograph of an exemplary toroidal DVBM mixer in accordance with the disclosed embodiments.

In one embodiment, the DVBM mixer is configured to mix at least a first liquid and a second liquid, the mixer comprising an inlet channel leading into a plurality of toroidal mixing elements arranged in series, wherein the plurality of toroidal mixing elements includes a first toroidal mixing element downstream of the inlet channel, and a second toroidal mixing element in fluidic communication with the first toroidal mixing element via a first neck region, and wherein the first toroidal mixing element defines a first neck angle between the inlet channel and the first neck region.

In one embodiment, the first neck angle is from 0 to 180 degrees.

In one embodiment, the first neck region has a length of 0.2 mm or greater.

In one embodiment, the plurality of mixing elements include channels having a hydrodynamic diameter of about 20 microns to about 2 mm.

In one embodiment, the mixer is sized and configured to mix the first liquid and the second liquid at a Reynolds number of less than 1000.

In one embodiment, the mixer includes two or more mixers in parallel, each mixer having a plurality of toroidal mixing elements.

In one embodiment, the first toroidal mixing element and the second toroidal mixing element define a mixing pair, and wherein the mixer includes a plurality of mixing pairs, and wherein each mixing pair is joined by a neck region at a neck angle.

In one embodiment, the first toroidal mixing element has a first leg of a first length and a second leg of a second length; and wherein the second toroidal mixing element has a first leg of a third length and a second leg of a fourth length.

In one embodiment, the first length is greater than the second length.

In one embodiment, the third length is greater than the fourth length.

In one embodiment, the ratio of the first length to the second length is about equal to the ratio of the third length to the fourth length.

In one embodiment, the first toroidal mixing element has a first leg of a first impedance and a second leg of a second impedance; and wherein the second toroidal mixing element has a first leg of a third impedance and a second leg of a fourth impedance.

In one embodiment, the first impedance is greater than the second impedance.

In one embodiment, the third impedance is greater than the fourth impedance.

In one embodiment, the ratio of the first impedance to the second impedance is about equal to the ratio of the third impedance to the fourth impedance.

In one embodiment, the mixer includes 2 to 20 toroidal mixing elements in series.

In one embodiment, the mixer includes 1 to 10 pairs of toroidal mixing elements in series.

In one embodiment, the toroidal mixing elements have an inner radius of about 0.1 mm to about 2 mm.

Also provided are methods of mixing a first liquid with a second liquid, comprising flowing the first liquid and the second liquid through a DVBM mixer according to the disclosed embodiments.

Definitions

Microfluidic

As used herein, the term "microfluidic" refers to a system or device for manipulating (e.g., flowing, mixing, etc.) a fluid sample including at least one channel having micron-scale dimensions (i.e., a dimension less than 1 mm).

Therapeutic Material

As used herein, the term "therapeutic material" is defined as a substance intended to furnish pharmacological activity or to otherwise have direct effect in the diagnosis, cure, mitigation, understanding, treatment or prevention of disease, or to have direct effect in restoring, correcting or modifying physiological functions. Therapeutic material includes but is not limited to small molecule drugs, nucleic acids, proteins, peptides, polysaccharides, inorganic ions and radionuclides.

Nanoparticles

As used herein, the term "nanoparticles" is defined as a homogeneous particle comprising more than one component material (for instance lipid, polymer etc.) that is used to encapsulate a therapeutic material and possesses a smallest dimension that is less than 250 nanometers. Nanoparticles include, but are not limited to, lipid nanoparticles and polymer nanoparticles.

Lipid Nanoparticles

In one embodiment, lipid nanoparticles, comprise:

(a) a core; and (b) a shell surrounding the core, wherein the shell comprises a phospholipid.

In one embodiment, the core comprises a lipid (e.g., a fatty acid triglyceride) and is solid. In another embodiment, the core is liquid (e.g., aqueous) and the particle is a vesicle, such as a liposomes. In one embodiment, the shell surrounding the core is a monolayer.

As noted above, in one embodiment, the lipid core comprises a fatty acid triglyceride. Suitable fatty acid triglycerides include C8-C20 fatty acid triglycerides. In one embodiment, the fatty acid triglyceride is an oleic acid triglyceride.

The lipid nanoparticle includes a shell comprising a phospholipid that surrounds the core. Suitable phospholipids include diacylphosphatidylcholines, diacylphosphatidylethanolamines, ceramides, sphingomyelins, dihydrosphingomyelins, cephalins, and cerebrosides. In one embodiment, the phospholipid is a C8-C20 fatty acid diacylphosphatidylcholine. A representative phospholipid is 1-palmitoyl-2-oleoyl phosphatidylcholine (POPC).

In certain embodiments, the ratio of phospholipid to fatty acid triglyceride is from 20:80 (mol:mol) to 60:40 (mol:mol). Preferably, the triglyceride is present in a ration greater than 40% and less than 80%.

In certain embodiments, the nanoparticle further comprises a sterol. Representative sterols include cholesterol. In one embodiment, the ratio of phospholipid to cholesterol is 55:45 (mol:mol). In representative embodiments, the nanoparticle includes from 55-100% POPC and up to 10 mol % PEG-lipid.

In other embodiments, the lipid nanoparticles of the disclosure may include one or more other lipids including phosphoglycerides, representative examples of which include phosphatidylcholine, phosphatidylethanolamine, phosphatidylserine, phosphatidylinositol, phosphatidic acid, palmitoyloleoylphosphatidylcholine, lyosphosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid and glycosphingolipid families are useful. Triacylglycerols are also useful.

Representative nanoparticles of the disclosure have a diameter from about 10 to about 100 nm. The lower diameter limit is from about 10 to about 15 nm.

The limit size lipid nanoparticles of the disclosure can include one or more therapeutic and/or diagnostic agents. These agents are typically contained within the particle core. The nanoparticles of the disclosure can include a wide variety of therapeutic and/or diagnostic agents.

Suitable therapeutic agents include chemotherapeutic agents (i.e., anti-neoplastic agents), anesthetic agents, beta-adrenaergic blockers, anti-hypertensive agents, anti-depressant agents, anti-convulsant agents, anti-emetic agents, anti-histamine agents, anti-arrhytmic agents, and anti-malarial agents.

Representative antineoplastic agents include doxorubicin, daunorubicin, mitomycin, bleomycin, streptozocin, vinblastine, vincristine, mechlorethamine, hydrochloride, melphalan, cyclophosphamide, triethylenethiophosphoramide, carmaustine, lomustine, semustine, fluorouracil, hydroxyurea, thioguanine, cytarabine, floxuridine, decarbazine, cisplatin, procarbazine, vinorelbine, ciprofloxacin, norfloxacin, paclitaxel, docetaxel, etoposide, bexarotene, teniposide, tretinoin, isotretinoin, sirolimus, fulvestrant, valrubicin, vindesine, leucovorin, irinotecan, capecitabine, gemcitabine, mitoxantrone hydrochloride, oxaliplatin, adriamycin, methotrexate, carboplatin, estramustine, and pharmaceutically acceptable salts and thereof.

In another embodiment, lipid nanoparticles, are nucleic-acid lipid nanoparticles.

The term "nucleic acid-lipid nanoparticles" refers to lipid nanoparticles containing a nucleic acid. The lipid nanoparticles include one or more cationic lipids, one or more second lipids, and one or more nucleic acids.

Cationic lipid. The lipid nanoparticles include a cationic lipid. As used herein, the term "cationic lipid" refers to a lipid that is cationic or becomes cationic (protonated) as the pH is lowered below the pK of the ionizable group of the lipid, but is progressively more neutral at higher pH values. At pH values below the pK, the lipid is then able to associate with negatively charged nucleic acids (e.g., oligonucleotides). As used herein, the term "cationic lipid" includes zwitterionic lipids that assume a positive charge on pH decrease.

The term "cationic lipid" refers to any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl)cholesterol (DC-Chol) and N-(1,2-dimyristyloxyprop-3-yl)-N,N-dimethyl-N-hydroxyethyl ammonium bromide (DMRIE). Additionally, a number of commercial preparations of cationic lipids are available which can be used in the present disclosure. These include, for example, LIPOFECTIN® (commercially available cationic liposomes comprising DOTMA and 1,2-dioleoyl-sn-3-phosphoethanolamine (DOPE), from GIBCO/BRL, Grand Island, NY); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, WI). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA).

In one embodiment, the cationic lipid is an amino lipid. Suitable amino lipids useful in the disclosure include those described in WO 2009/096558, incorporated herein by reference in its entirety. Representative amino lipids include 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA·Cl), 1,2-dilinoleoyl-3-trimethylaminopropane chloride salt (DLin-TAP·Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

Suitable amino lipids include those having the formula:

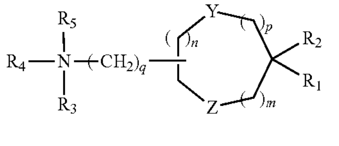

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;

$R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or $C_1$-$C_6$ alkyl;

m, n, and p are either the same or different and independently either 0 or 1 with the proviso that m, n, and p are not simultaneously 0;

q is 0, 1, 2, 3, or 4; and

Y and Z are either the same or different and independently O, S, or NH.

In one embodiment, $R_1$ and $R_2$ are each linoleyl, and the amino lipid is a dilinoleyl amino lipid. In one embodiment, the amino lipid is a dilinoleyl amino lipid.

A representative useful dilinoleyl amino lipid has the formula:

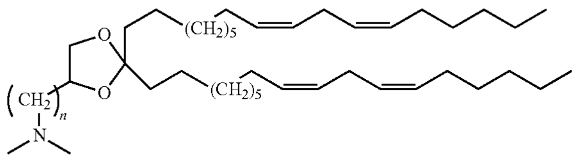

DLin-K-DMA wherein n is 0, 1, 2, 3, or 4.

In one embodiment, the cationic lipid is a DLin-K-DMA. In one embodiment, the cationic lipid is DLin-KC2-DMA (DLin-K-DMA above, wherein n is 2).

Other suitable cationic lipids include cationic lipids, which carry a net positive charge at about physiological pH, in addition to those specifically described above, N,N-dioleyl-N,N-dimethylammonium chloride (DODAC); N-(2,3-dioleyloxy)propyl-N,N—N-triethylammonium chloride (DOTMA); N,N-distearyl-N,N-dimethylammonium bromide (DDAB); N-(2,3-dioleoyloxy)propyl)-N,N,N-trimethylammonium chloride (DOTAP); 1,2-dioleyloxy-3-trimethylaminopropane chloride salt (DOTAP·Cl); 3β-(N—(N',N'-dimethylaminoethane)carbamoyl)cholesterol (DC-Chol), N-(1-(2,3-dioleoyloxy)propyl)-N-2-(sperminecarboxamido)ethyl)-N,N-dimethylammonium trifluoracetate (DOSPA), dioctadecylamidoglycyl carboxyspermine (DOGS), 1,2-dioleoyl-3-dimethylammonium propane (DODAP), N,N-dimethyl-2,3-dioleoyloxy)propylamine (DODMA), and N-(1,2-dimyristyloxyprop-3-yl)-N,N-dimethyl-N-hydroxyethyl ammonium bromide (DMRIE). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

The cationic lipid is present in the lipid particle in an amount from about 30 to about 95 mole percent. In one embodiment, the cationic lipid is present in the lipid particle in an amount from about 30 to about 70 mole percent. In one embodiment, the cationic lipid is present in the lipid particle in an amount from about 40 to about 60 mole percent.

In one embodiment, the lipid particle includes ("consists of") only one or more cationic lipids and one or more nucleic acids.

Second lipids. In certain embodiments, the lipid nanoparticles include one or more second lipids. Suitable second lipids stabilize the formation of nanoparticles during their formation.

The term "lipid" refers to a group of organic compounds that are esters of fatty acids and are characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

Suitable stabilizing lipids include neutral lipids and anionic lipids.

Neutral Lipid. The term "neutral lipid" refers to any one of a number of lipid species that exist in either an uncharged or neutral zwitterionic form at physiological pH. Representative neutral lipids include diacylphosphatidylcholines, diacylphosphatidylethanolamines, ceramides, sphingomyelins, dihydrosphingomyelins, cephalins, and cerebrosides.

Exemplary lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), and 1,2-dielaidoyl-sn-glycero-3-phophoethanolamine (transDOPE).

In one embodiment, the neutral lipid 1,2-distearoyl-sn-glycero-3-phosphocholine (DSPC).

Anionic Lipid. The term "anionic lipid" refers to any lipid that is negatively charged at physiological pH. These lipids include phosphatidylglycerol, cardiolipin, diacylphosphatidylserine, diacylphosphatidic acid, N-dodecanoylphosphatidylethanolamines, N-succinylphosphatidylethanolamines, N-glutarylphosphatidylethanolamines, lysylphosphatidylglycerols, palmitoyloleyolphosphatidylglycerol (POPG), and other anionic modifying groups joined to neutral lipids.

Other suitable lipids include glycolipids (e.g., monosialoganglioside $GM_1$). Other suitable second lipids include sterols, such as cholesterol.

Polyethylene glycol-lipids. In certain embodiments, the second lipid is a polyethylene glycol-lipid. Suitable polyethylene glycol-lipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. In one embodiment, the polyethylene glycol-lipid is N-[(methoxy poly(ethylene glycol)$_{2000}$)carbamyl]-1,2-dimyristyloxlpropyl-3-amine (PEG-c-DMA). In one embodiment, the polyethylene glycol-lipid is PEG-c-DOMG).

In certain embodiments, the second lipid is present in the lipid particle in an amount from about 0.5 to about 10 mole percent. In one embodiment, the second lipid is present in the lipid particle in an amount from about 1 to about 5 mole percent. In one embodiment, the second lipid is present in the lipid particle in about 1 mole percent.

Nucleic Acids. The lipid nanoparticles of the present disclosure are useful for the systemic or local delivery of nucleic acids. As described herein, the nucleic acid is incorporated into the lipid particle during its formation.

As used herein, the term "nucleic acid" is meant to include any oligonucleotide or polynucleotide. Fragments containing up to 50 nucleotides are generally termed oligonucleotides, and longer fragments are called polynucleotides. In particular embodiments, oligonucleotides of the present disclosure are 20-50 nucleotides in length. In the context of this disclosure, the terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases. Oligonucleotides are classified as deoxyribooligonucleotides or ribooligonucleotides. A deoxyribooligonucleotide consists of a 5-carbon sugar called deoxyhbose joined covalently to phosphate at the 5' and 3' carbons of this sugar to form an alternating, unbranched polymer. A ribooligonucleotide consists of a similar repeating structure where the 5-carbon sugar is ribose. The nucleic acid that is present in a lipid particle according to this disclosure includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include antisense oligonucleotides, ribozymes, microRNA, and triplex-forming oligonucleotides.

In one embodiment, the polynucleic acid is an antisense oligonucleotide. In certain embodiments, the nucleic acid is an antisense nucleic acid, a ribozyme, tRNA, snRNA, siRNA, shRNA, ncRNA, miRNA, mRNA, lncRNA, pre-condensed DNA, or an aptamer.

The term "nucleic acids" also refers to ribonucleotides, deoxynucleotides, modified ribonucleotides, modified deoxyribonucleotides, modified phosphate-sugar-backbone oligonucleotides, other nucleotides, nucleotide analogs, and combinations thereof, and can be single stranded, double stranded, or contain portions of both double stranded and single stranded sequence, as appropriate.

The term "nucleotide", as used herein, generically encompasses the following terms, which are defined below: nucleotide base, nucleoside, nucleotide analog, and universal nucleotide.

The term "nucleotide base", as used herein, refers to a substituted or unsubstituted parent aromatic ring or rings. In some embodiments, the aromatic ring or rings contain at least one nitrogen atom. In some embodiments, the nucleotide base is capable of forming Watson-Crick and/or Hoogsteen hydrogen bonds with an appropriately complementary nucleotide base. Exemplary nucleotide bases and analogs thereof include, but are not limited to, purines such as 2-aminopurine, 2,6-diaminopurine, adenine (A), ethenoadenine, N6-2-isopentenyladenine (6iA), N6-2-isopentenyl-2-methylthioadenine (2ms6iA), N6-methyladenine, guanine (G), isoguanine, N2-dimethylguanine (dmG), 7-methylguanine (7 mG), 2-thiopyrimidine, 6-thioguanine (6sG) hypoxanthine and O6-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, O4-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); In some embodiments, nucleotide bases are universal nucleotide bases. Additional exemplary nucleotide bases can be found in Fasman, 1989, Practical Handbook of Biochemistry and Molecular Biology, pp. 385-394, CRC Press, Boca Raton, Fla., and the references cited therein. Further examples of universal bases can be found for example in Loakes, N. A. R. 2001, vol 29:2437-2447 and Seela N. A. R. 2000, vol 28:3224-3232.

The term “nucleoside”, as used herein, refers to a compound having a nucleotide base covalently linked to the C-1' carbon of a pentose sugar. In some embodiments, the linkage is via a heteroaromatic ring nitrogen. Typical pentose sugars include, but are not limited to, those pentoses in which one or more of the carbon atoms are each independently substituted with one or more of the same or different —R, —OR, —NRR or halogen groups, where each R is independently hydrogen, (C1-C6) alkyl or (C5-C14) aryl. The pentose sugar may be saturated or unsaturated. Exemplary pentose sugars and analogs thereof include, but are not limited to, ribose, 2'-deoxyribose, 2'-(C1-C6)alkoxyribose, 2'-(C5-C14)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose. Also see, e.g., 2'-O-methyl, 4'-.alpha.-anomeric nucleotides, 1'-.alpha.-anomeric nucleotides (Asseline (1991) Nucl. Acids Res. 19:4067-74), 2'-4'- and 3'-4'-linked and other “locked” or “LNA”, bicyclic sugar modifications (WO 98/22489; WO 98/39352; WO 99/14226). “LNA” or “locked nucleic acid” is a DNA analogue that is conformationally locked such that the ribose ring is constrained by a methylene linkage between the 2'-oxygen and the 3'- or 4'-carbon. The conformation restriction imposed by the linkage often increases binding affinity for complementary sequences and increases the thermal stability of such duplexes.

Sugars include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleobase is purine, e.g., A or G, the ribose sugar is attached to the N9-position of the nucleobase. When the nucleobase is pyrimidine, e.g., C, T or U, the pentose sugar is attached to the N1-position of the nucleobase (Kornberg and Baker, (1992) DNA Replication, 2.sup.nd Ed., Freeman, San Francisco, Calif.).

One or more of the pentose carbons of a nucleoside may be substituted with a phosphate ester. In some embodiments, the phosphate ester is attached to the 3'- or 5'-carbon of the pentose. In some embodiments, the nucleosides are those in which the nucleotide base is a purine, a 7-deazapurine, a pyrimidine, a universal nucleotide base, a specific nucleotide base, or an analog thereof.

The term “nucleotide analog”, as used herein, refers to embodiments in which the pentose sugar and/or the nucleotide base and/or one or more of the phosphate esters of a nucleoside may be replaced with its respective analog. In some embodiments, exemplary pentose sugar analogs are those described above. In some embodiments, the nucleotide analogs have a nucleotide base analog as described above. In some embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, and may include associated counterions. Other nucleic acid analogs and bases include for example intercalating nucleic acids (INAs, as described in Christensen and Pedersen, 2002), and AEGIS bases (Eragen, U.S. Pat. No. 5,432,272). Additional descriptions of various nucleic acid analogs can also be found for example in (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048. Other nucleic analogs comprise phosphorodithioates (Briu et al., J. Am. Chem. Soc. 111:2321 (1989), O-methylphophoroamidite linkages (see Eckstein, Oligonucleotides and Analogues: A Practical Approach, Oxford University Press), those with positive backbones (Denpcy et al., Proc. Natl. Acad. Sci. USA 92:6097 (1995); non-ionic backbones (U.S. Pat. Nos. 5,386,023, 5,386,023, 5,637,684, 5,602,240, 5,216,141, and 4,469,863. Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (194): Chapters 2 and 3, ASC Symposium Series 580, “Carbohydrate Modifications in Antisense Research”, Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, “Carbohydrate Modifications in Antisense Research”, Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are also described in Rawls, C & E News Jun. 2, 1997 page 35.

The term “universal nucleotide base” or “universal base”, as used herein, refers to an aromatic ring moiety, which may or may not contain nitrogen atoms. In some embodiments, a universal base may be covalently attached to the C-1' carbon of a pentose sugar to make a universal nucleotide. In some embodiments, a universal nucleotide base does not hydrogen bond specifically with another nucleotide base. In some embodiments, a universal nucleotide base hydrogen bonds with nucleotide base, up to and including all nucleotide bases in a particular target polynucleotide. In some embodiments, a nucleotide base may interact with adjacent nucleotide bases on the same nucleic acid strand by hydrophobic stacking. Universal nucleotides include, but are not limited to, deoxy-7-azaindole triphosphate (d7AITP), deoxyisocarbostyril triphosphate (dICSTP), deoxypropynylisocarbostyril triphosphate (dPICSTP), deoxymethyl-7-azaindole triphosphate (dM7AITP), deoxyImPy triphosphate (dImPyTP), deoxyPP triphosphate (dPPTP), or deoxypropynyl-7-azaindole triphosphate (dP7AITP). Further examples of such universal bases can be found, inter alia, in Published U.S. application Ser. No. 10/290,672, and U.S. Pat. No. 6,433,134.

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, e.g., 3'-5' and 2'-5', inverted linkages, e.g., 3'-3' and 5'-5', branched structures, or internucleotide analogs. Polynucleotides have associated counter ions, such as H+, NH4+, trialkylammonium, Mg2+, Na+, and the like. A polynucleotide may be composed entirely of deoxyribonucleotides, entirely of ribonucleotides, or chimeric mixtures thereof. Polynucleotides may be comprised of internucleotide, nucleobase and/or sugar analogs. Polynucleotides typically range in size from a few monomeric units, e.g., 3-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, and "T" denotes thymidine, unless otherwise noted.

As used herein, "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methlylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobase include those nucleobases illustrated in FIGS. 2(A) and 2(B) of Buchardt et al. (WO92/20702 or WO92/20703).

As used herein, "nucleobase sequence" means any segment, or aggregate of two or more segments (e.g. the aggregate nucleobase sequence of two or more oligomer blocks), of a polymer that comprises nucleobase-containing subunits. Non-limiting examples of suitable polymers or polymers segments include oligodeoxynucleotides (e.g. DNA), oligoribonucleotides (e.g. RNA), peptide nucleic acids (PNA), PNA chimeras, PNA combination oligomers, nucleic acid analogs and/or nucleic acid mimics.

As used herein, "polynucleobase strand" means a complete single polymer strand comprising nucleobase subunits. For example, a single nucleic acid strand of a double stranded nucleic acid is a polynucleobase strand.

As used herein, "nucleic acid" is a nucleobase sequence-containing polymer, or polymer segment, having a backbone formed from nucleotides, or analogs thereof.

Preferred nucleic acids are DNA and RNA.

As used herein, nucleic acids may also refer to "peptide nucleic acid" or "PNA" means any oligomer or polymer segment (e.g. block oligomer) comprising two or more PNA subunits (residues), but not nucleic acid subunits (or analogs thereof), including, but not limited to, any of the oligomer or polymer segments referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470; all of which are herein incorporated by reference. The term "peptide nucleic acid" or "PNA" shall also apply to any oligomer or polymer segment comprising two or more subunits of those nucleic acid mimics described in the following publications: Lagriffoul et al., Bioorganic & Medicinal Chemistry Letters, 4: 1081-1082 (1994); Petersen et al., Bioorganic & Medicinal Chemistry Letters, 6: 793-796 (1996); Diderichsen et al., Tett. Lett. 37: 475-478 (1996); Fujii et al., Bioorg. Med. Chem. Lett. 7: 637-627 (1997); Jordan et al., Bioorg. Med. Chem. Lett. 7: 687-690 (1997); Krotz et al., Tett. Lett. 36: 6941-6944 (1995); Lagriffoul et al., Bioorg. Med. Chem. Lett. 4: 1081-1082 (1994); Diederichsen, U., Bioorganic & Medicinal Chemistry Letters, 7: 1743-1746 (1997); Lowe et al., J. Chem. Soc. Perkin Trans. 1, (1997) 1: 539-546; Lowe et J. Chem. Soc. Perkin Trans. 11: 547-554 (1997); Lowe et al., J. Chem. Soc. Perkin Trans. 11:555-560 (1997); Howarth et al., J. Org. Chem. 62: 5441-5450 (1997); Altmann, K-H et al., Bioorganic & Medicinal Chemistry Letters, 7: 1119-1122 (1997); Diederichsen, U., Bioorganic & Med. Chem. Lett., 8: 165-168 (1998); Diederichsen et al., Angew. Chem. Int. Ed., 37: 302-305 (1998); Cantin et al., Tett. Lett., 38: 4211-4214 (1997); Ciapetti et al., Tetrahedron, 53: 1167-1176 (1997); Lagriffoule et al., Chem. Eur. J., 3: 912-919 (1997); Kumar et al., Organic Letters 3(9): 1269-1272 (2001); and the Peptide-Based Nucleic Acid Mimics (PENAMS) of Shah et al. as disclosed in WO96/04000.

Polymer Nanoparticles

The term "polymer nanoparticles" refers to polymer nanoparticles containing a therapeutic material. Polymer nanoparticles have been developed using, a wide range of materials including, but not limited to: synthetic homopolymers such as polyethylene glycol, polylactide, polyglycolide, poly(lactide-coglycolide), polyacrylates, polymethacrylates, poly caprolactone, polyorthoesters, polyanhydrides, polylysine, polyethyleneimine; synthetic copolymers such as poly(lactide-coglycolide), poly(lactide)-poly(ethylene glycol), poly(lactide-co-glycolide)-poly(ethylene glycol), poly(caprolactone)-poly(ethylene glycol); natural polymers such as cellulose, chitin, and alginate, as well as polymer-therapeutic material conjugates As used herein, the term "polymer" refers to compounds of usually high molecular weight built up chiefly or completely from a large number of similar units bonded together. Such polymers include any of numerous natural, synthetic and semi-synthetic polymers.

The term "natural polymer" refers to any number of polymer species derived from nature. Such polymers include, but are not limited to the polysaccharides, cellulose, chitin, and alginate.

The term "synthetic polymer" refers to any number of synthetic polymer species not found in Nature. Such synthetic polymers include, but are not limited to, synthetic homopolymers and synthetic copolymers.

Synthetic homopolymers include, but are not limited to, polyethylene glycol, polylactide, polyglycolide, polyacrylates, polymethacrylates, poly caprolactone, polyorthoesters, polyanhydrides, polylysine, and polyethyleneimine.

"Synthetic copolymer" refers to any number of synthetic polymer species made up of two or more synthetic homopolymer subunits. Such synthetic copolymers include, but are not limited to, poly(lactide-co-glycolide), poly(lactide)-poly (ethylene glycol), poly(lactide-co-glycolide)-poly(ethylene glycol), and poly(caprolactone)-poly(ethylene glycol).

The term "semi-synthetic polymer" refers to any number of polymers derived by the chemical or enzymatic treatment of natural polymers. Such polymers include, but are not limited to, carboxymethyl cellulose, acetylated carboxymethylcellulose, cyclodextrin, chitosan and gelatin.

As used herein, the term "polymer conjugate" refers to a compound prepared by covalently, or non-covalently conjugating one or more molecular species to a polymer. Such polymer conjugates include, but are not limited to, polymer-therapeutic material conjugates.

Polymer-therapeutic material conjugate refers to a polymer conjugate where one or more of the conjugated molecular species is a therapeutic material. Such polymer-therapeutic material conjugates include, but are not limited to, polymer-drug conjugates.

"Polymer-drug conjugate" refers to any number of polymer species conjugated to any number of drug species. Such polymer drug conjugates include, but are not limited to, acetyl methylcellulose-polyethylene glycol-docetaxol.

As used herein, the term "about" indicates that the associated value can be modified, unless otherwise indicated, by plus or minus five percent (+/−5%) and remain within the scope of the embodiments disclosed.

The following example is included for the purpose of illustrating, not limiting, the described embodiments.

EXAMPLES

Figure 4:
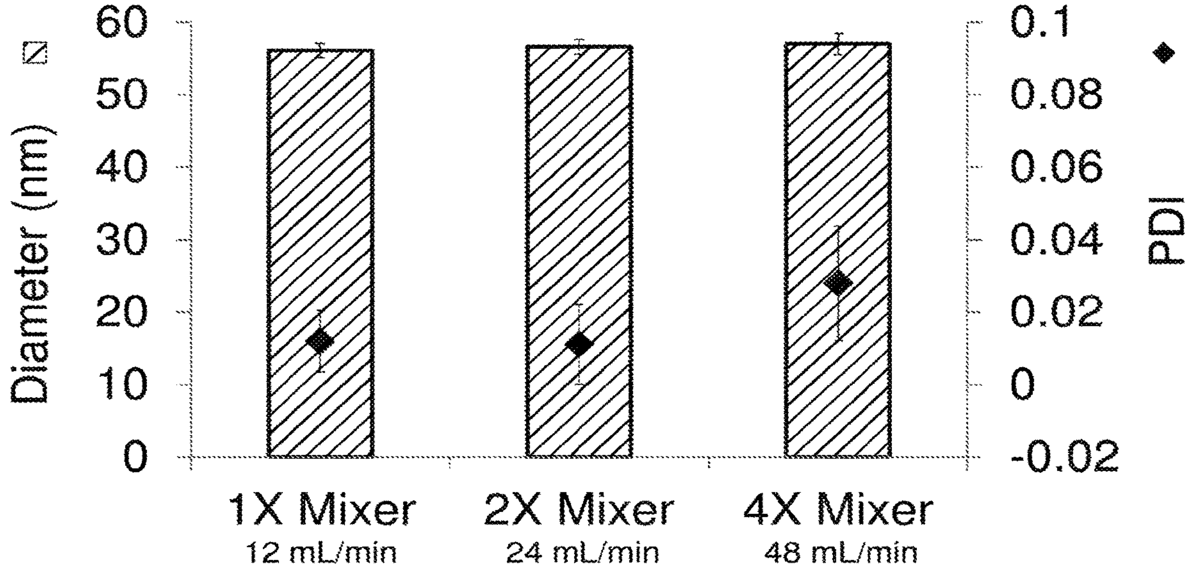
FIG. 4 shows particle diameter (nm) and polydispersity index (PDI) for representative siRNA-Lipid Nanoparticles (siRNA-LNP) as a function of four single microfluidic mixer devices arrayed in parallel using a manifold, or four microfluidic mixers arrayed in parallel in the representative single device illustrated in FIG. 3. The siRNA-LNP were composed of 1,17-bis(2-octylcyclopropyl)heptadecan-9-yl 4-(dimethylamino)butanoate/DSPC/Chol/PEG-c-DMA at mole ratios of 50:10:38.5:1.5 and a siRNA-total lipid ratio of 0.06 wt/wt, and the nanoparticles were produced using the illustrative continuous flow system shown in FIG. 2 with either four single microfluidic mixer device arrayed in parallel using a manifold (4× Manifold), or four microfluidic mixers arrayed in parallel in a single device illustrated in FIG. 3 (4× On-Chip). The total flow rates through the microfluidic device are shown in the legend. Error bars represent the standard deviation of the mean.

Example 1: siRNA-Lipid Nanoparticles (siRNA-LNP) Manufactured Using Four Single Microfluidic Mixer Devices Arrayed in Parallel Using a Manifold, or Four Microfluidic Mixers Arrayed in Parallel in a Single Device In this example, the siRNA-LNP produced using four single microfluidic mixer devices in parallel using a manifold is compared to the siRNA-LNP produced using four microfluidic mixers arrayed in parallel in a single device (FIG. 3). The purpose of this example is to demonstrate that there are on-device and off-device methods of arraying microfluidic mixer. The fluid driving pumps were operated under the same process conditions, with identical nanoparticle forming materials, and tests were conducted on the each method of arraying. The results in FIG. 4 show similar siRNA-LNP produced using the two methods of arraying, and the siRNA-LNP is not affected by the method of arraying. This example significantly demonstrates the possibility of using either, or both, on-device and off-device methods of arraying to significantly increase the number of mixers in a single system. Using both on-device and off-device methods of arraying yields a two dimensional method of arraying microfluidic mixers.

FIG. 4 shows particle diameter (nm) and polydispersity index (PDI) for representative siRNA-Lipid Nanoparticles (siRNA-LNP) as a function of four single microfluidic mixer devices arrayed in parallel using a manifold, or four microfluidic mixers arrayed in parallel in the representative single device illustrated in FIG. 3. The siRNA-LNP were composed of 1,17-bis(2-octylcyclopropyl)heptadecan-9-yl 4-(dimethylamino)butanoate/DSPC/Chol/PEG-c-DMA at mole ratios of 50:10:38.5:1.5 and a siRNA-total lipid ratio of 0.06 wt/wt, and the nanoparticles were produced using the illustrative continuous flow system shown in FIG. 2 with either four single microfluidic mixer device arrayed in parallel using a manifold (4× Manifold), or four microfluidic mixers arrayed in parallel in a single device illustrated in FIG. 3 (4× On-Chip). The total flow rates through the microfluidic device are shown in the legend. Error bars represent the standard deviation of the mean.

In this Example, 0.231 mg/mL siRNA in 50 mM sodium acetate buffer (pH 4.0) and lipid mix (12.5 mM 1,17-bis(2-octylcyclopropyl)heptadecan-9-yl 4-(dimethylamino)butanoate/DSPC/Chol/PEG-c-DMA at mole ratios of 50:10:38.5:1.5 in ethanol) in separate syringes were loaded into independent Harvard PHD Ultra syringe pumps (Harvard Apparatus, Holliston, MA). The siRNA-total lipid ratio was 0.06 wt/wt. Mixing volumes ratios of siRNA to lipid mix was 3:1, with 5 mL total volume processed per mixer (i.e., total formulation volumes: 1×=5 mL, 2×=10 mL, 4×=20 mL). Flow rate per mixer was 12 mL/min at siRNA to lipid mix flow rate ratio of 3:1 (i.e., 9 mL/min siRNA and 3 mL/min lipid mix in 1×). The first 2 mL of volume collected from the mixer outlet at the beginning of each formulation run was discarded as waste, and the remaining volume was collected as the sample. The 1 mL of the collected sample was further diluted into 3 mL of Dulbecco's Phosphate Buffered Saline (without calcium and without magnesium) before particle sizing.

Particle size measurement was performed as follows: siRNA-LNP were diluted to appropriate concentration with Dulbecco's Phosphate Buffered Saline (without calcium and without magnesium) and mean particle size (intensity-weighted) was determined by dynamic light scattering (DLS) using a Malvern Zetasizer Nano ZS two angle particle sizer (Malvern Instruments Ltd., Malvern, Worcestershire, UK).

Example 2: siRNA-Lipid Nanoparticles (siRNA-LNP) Manufactured Using Eight Single Microfluidic Mixer Devices Arrayed in Parallel Using a Manifold In this example, 520 mL volume of siRNA-LNP was produced using eight single microfluidic mixer devices arrayed in parallel using an external manifold. Each mixer in the array was identical, thus the process conditions for forming siRNA-LNP in each mixer was identical. The purpose of this experiment was to demonstrate the effect of a large number of parallel mixers on siRNA-LNP size and quality. This example significantly demonstrates the successful utilization of a large number of microfluidic mixers used in parallel in the same system to produce a large volume batch of siRNA-LNP using an exemplary system as disclosed herein.

Figure 5:
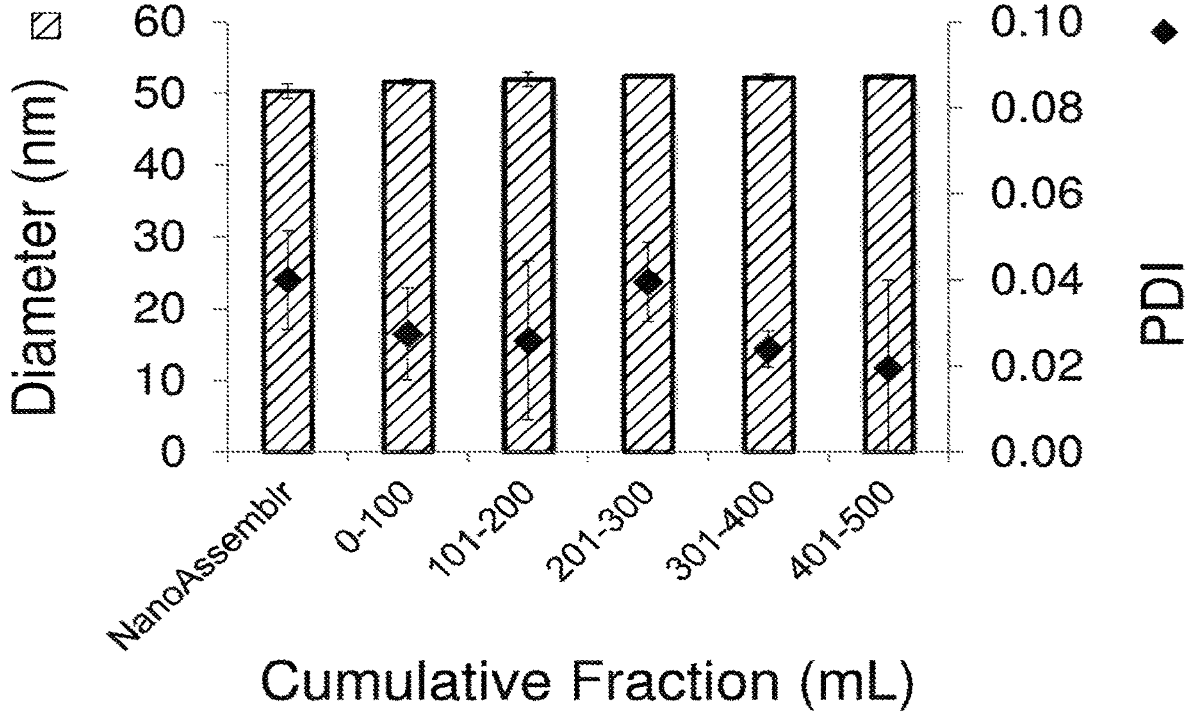
FIG. 5 shows particle diameter (nm) and polydispersity index (PDI) for representative siRNA-Lipid Nanoparticles (siRNA-LNP) as a function of the manufactured volume. The siRNA-LNP were composed of 1,17-bis(2-octylcyclopropyl)heptadecan-9-yl 4-(dimethylamino)butanoate/DSPC/Chol/PEG-c-DMA at mole ratios of 50:10:38.5:1.5 and a siRNA-total lipid ratio of 0.06 wt/wt, and the nanoparticles were produced using the illustrative continuous flow system shown in FIG. 2 with eight single microfluidic mixer device arrayed in parallel using a manifold. Nanoparticles were sampled every 100 mL from 0 mL to 500 mL and the results compared to a 2 mL preparation of the same siRNA-LNP prepared using the NanoAssemblr™ Benchtop Instrument. The NanoAssemblr™ Benchtop Instrument is commercially available laboratory apparatus that uses microfluidics to manufacture fixed volume batches of nanoparticles. Error bars represent the standard deviation of the mean.

FIG. 5 shows particle diameter (nm) and polydispersity index (PDI) for representative siRNA-Lipid Nanoparticles (siRNA-LNP) as a function of the manufactured volume. The siRNA-LNP were composed of 1,17-bis(2-octylcyclopropyl)heptadecan-9-yl 4-(dimethylamino)butanoate/DSPC/Chol/PEG-c-DMA at mole ratios of 50:10:38.5:1.5 and a siRNA-total lipid ratio of 0.06 wt/wt, and the nanoparticles were produced using the illustrative continuous flow system shown in FIG. 2 with eight single microfluidic mixer device arrayed in parallel using a manifold. Nanoparticles were sampled every 100 mL from 0 mL to 500 mL and the results compared to a 2 mL preparation of the same siRNA-LNP prepared using the NanoAssemblr™ Benchtop Instrument. The NanoAssemblr™ Benchtop Instrument is commercially available laboratory apparatus that uses microfluidics to manufacture fixed volume batches of nanoparticles. Error bars represent the standard deviation of the mean.

In this Example, 0.231 mg/mL siRNA in 50 mM sodium acetate buffer (pH 4.0) and lipid mix (12.5 mM 1,17-bis(2- octylcyclopropyl)heptadecan-9-yl 4-(dimethylamino)butanoate/DSPC/Chol/PEG-c-DMA at mole ratios of 50:10:38.5:1.5 in ethanol) loaded in separate Flash 100 metering pump (Scientific Systems, Inc., State College, PA). The siRNA-total lipid ratio was 0.06 wt/wt. Mixing volumes ratios of siRNA to lipid mix was 3:1, with 65 mL total volume processed per mixer (ie: total formulation volumes in 8×=520 mL). Flow rate per mixer was 12 mL/min at siRNA to lipid mix flow rate ratio of 3:1 (total flow rate=96 ml/min, thus flow rates for siRNA and lipid mix were 72 mL/min and 24 mL/min respectively). The first 20 mL of volume collected from the mixer outlet at the beginning the formulation run was discarded as waste, and the remaining volume was collected as the sample. After the first 20 mL priming waste was collected, the particle formulation was diluted in-line with Dulbecco's Phosphate Buffered Saline (without calcium and without magnesium), 1 part particle solution to 3 part DPBS, driven by a Masterflex L/S peristaltic pump with dual Easy-load II pump heads (Cole-Parmer Instrument Company, Montreal, QC, Canada). The resulting particle formulation was collected in aliquots and sized.

While illustrative embodiments have been illustrated and described, it will be appreciated that various changes can be made therein without departing from the spirit and scope of the invention.

The embodiments of the invention in which an exclusive property or privilege is claimed are defined as follows:

1. A mixer configured to mix a first liquid and a second liquid, the mixer comprising:
- a first toroidal mixing element having a first leg having a first hydrodynamic diameter defining a first fluidic impedance and a second leg having a second hydrodynamic diameter defining a second fluidic impedance, the first leg and the second leg leading into and being fluidly coupled to a first neck region;
- a second toroidal mixing element having a third leg and a fourth leg fluidly coupled to the first neck region, the third leg and the fourth leg leading into and being fluidly coupled to a second neck region, wherein the third leg has a third hydrodynamic diameter defining a third fluidic impedance and the fourth leg has a fourth hydrodynamic diameter defining a fourth fluidic impedance that differs from the third fluidic impedance; and
- a third toroidal mixing element having a fifth leg and a sixth leg fluidly coupled to the second neck region, the fifth leg and the sixth leg leading into and being fluidly coupled to an outlet, wherein the fifth leg has a fifth hydrodynamic diameter defining a fifth fluidic impedance and the sixth leg has a sixth hydrodynamic diameter defining a sixth fluidic impedance,
- wherein the first leg, the third leg, and the fifth leg are located on a first side of the mixer and the second leg, the fourth leg, and the sixth leg are located on a second side of the mixer,
- wherein at least two pairs of: a first pair of the first and second legs; a second pair of the third and fourth legs; and a third pair of the fifth and sixth legs are asymmetrical, and
- wherein a first ratio of the first fluidic impedance to the second fluidic impedance differs from either a second ratio of the third fluidic impedance to the fourth fluidic impedance or a third ratio of the fifth fluidic impedance to the sixth fluidic impedance.

2. The mixer of 1, wherein the first ratio is about 1:1 to about 10:1.

3. The mixer of claim 1, wherein the first ratio is different than the second ratio and wherein the second ratio is different than the third ratio.

4. The mixer of claim 1, wherein the second ratio is an inverse of the first ratio.

5. The mixer of claim 1, wherein the first fluidic impedance is different than at least one of the second and third fluidic impedances.

6. The mixer of claim 1, wherein the first leg has a first length, the second leg has a second length, and the third leg has a third length, wherein the first length is different than at least one of the second and third lengths.

7. The mixer of claim 1, wherein the first leg has a first cross section, the second leg has a second cross section, and the third leg has a third cross section, wherein the first cross section is greater than at least one of the second and third cross sections.

8. The mixer of claim 1, wherein the first fluidic impedance equals the fourth fluidic impedance, and the second fluidic impedance equals the third fluidic impedance.

9. The mixer of claim 1, wherein at least one of the first toroidal mixing element or the second toroidal mixing element has a variable radius.

10. The mixer of claim 1, wherein the first toroidal mixing element has a first radius and the second toroidal mixing element has a second radius that differs from the first radius.

11. A system for continuous flow operation of a microfluidic chip, the system comprising:

(1) the microfluidic chip, comprising:

(a) a mixer configured to mix a first solution and a second solution to provide a mixed solution at a mixer outlet, the mixer comprising:

(i) a first toroidal mixing element having a first leg having a first hydrodynamic diameter defining a first fluidic impedance and a second leg having a second hydrodynamic diameter defining a second fluidic impedance, the first leg and the second leg leading into and being fluidly coupled to a first neck region;

(ii) a second toroidal mixing element having a third leg and a fourth leg fluidly coupled to the first neck region, the third leg and the fourth leg leading into and being fluidly coupled to a second neck region, wherein the third leg has a third hydrodynamic diameter defining a third fluidic impedance and the fourth leg has a fourth hydrodynamic diameter defining a fourth fluidic impedance that differs from the third fluidic impedance;

(iii) a third toroidal mixing element having a fifth leg and a sixth leg fluidly coupled to the second neck region, the fifth leg and the sixth leg leading into and being fluidly coupled to the mixer outlet, wherein the fifth leg has a fifth hydrodynamic diameter defining a fifth fluidic impedance and the sixth leg has a sixth hydrodynamic diameter defining a sixth fluidic impedance, wherein the first leg, the third leg, and the fifth leg are located on a first side of the mixer and the second leg, the fourth leg, and the sixth leg are located on a second side of the mixer, wherein at least two pairs of: a first pair of the first and second legs; a second pair of the third and fourth legs; and a third pair of the fifth and sixth legs are asymmetrical, and wherein a first ratio of the first fluidic impedance to the second fluidic impedance differs from either a second ratio of the third fluidic impedance to the fourth fluidic impedance or a third ratio of the fifth fluidic impedance to the sixth fluidic impedance; and (b) a chip outlet in fluid communication with the mixer outlet through a mixed solution microchannel;

(2) a first fluid driver configured to continuously drive the first solution into the mixer;

(3) a second fluid driver configured to continuously drive the second solution into the mixer; and (4) a system outlet in fluid communication with the chip outlet.

12. The system of claim 11, wherein the first ratio is about 1:1 to about 10:1.

13. The system of claim 11, wherein the first ratio is different than the second ratio and wherein the second ratio is different than the third ratio.

14. The system of claim 11, wherein the second ratio is an inverse of the first ratio.

15. The system of claim 11, wherein the first fluidic impedance is different than at least one of the second and third fluidic impedances.

16. The system of claim 11, wherein the first leg has a first length, the second leg has a second length, and the third leg has a third length, wherein the first length is different than at least one of the second and third lengths.

17. The system of claim 11, wherein the first leg has a first cross section, the second leg has a second cross section, and the third leg has a third cross section, wherein the first cross section is greater than at least one of the second and third cross sections.

18. The system of claim 11, wherein the first fluidic impedance equals the fourth fluidic impedance, and the second fluidic impedance equals the third fluidic impedance.

19. The system of claim 11, wherein at least one of the first toroidal mixing element or the second toroidal mixing element has a variable radius.

20. The system of claim 11, wherein the first toroidal mixing element has a first radius and the second toroidal mixing element has a second radius that differs from the first radius.

* * * * *